(12) United States Patent
Yun et al.

(10) Patent No.: US 7,676,269 B2
(45) Date of Patent: Mar. 9, 2010

(54) TREATMENT OF FEMALE FERTILITY CONDITIONS THROUGH MODULATION OF THE AUTONOMIC NERVOUS SYSTEM

(75) Inventors: Anthony Joonkyoo Yun, Palo Alto, CA (US); Patrick Yuarn-Bor Lee, Piedmont, CA (US)

(73) Assignee: Palo Alto Investors, Palo Alto, CA (US)

( * ) Notice: Subject to any disclaimer, the term of this patent is extended or adjusted under 35 U.S.C. 154(b) by 439 days.

(21) Appl. No.: 10/748,976

(22) Filed: Dec. 29, 2003

(65) Prior Publication Data

US 2005/0143788 A1 Jun. 30, 2005

(51) Int. Cl.
*A61N 1/36* (2006.01)
(52) U.S. Cl. ............................... 607/39; 607/2
(58) Field of Classification Search .............. 607/39, 607/2
See application file for complete search history.

(56) References Cited

U.S. PATENT DOCUMENTS

| | | | |
|---|---|---|---|
| 4,339,384 A * | 7/1982 | Maillard et al. ............. 548/525 |
| 5,188,104 A | 2/1993 | Wernicke et al. | |
| 5,215,086 A | 6/1993 | Terry, Jr. et al. | |
| 5,231,988 A | 8/1993 | Wernicke et al. | |
| 5,263,480 A | 11/1993 | Wernicke et al. | |
| 5,269,303 A | 12/1993 | Wernicke et al. | |
| 5,330,515 A | 7/1994 | Rutecki et al. | |
| 5,335,657 A | 8/1994 | Terry, Jr. et al. | |
| 5,437,285 A * | 8/1995 | Verrier et al. ............... 600/515 |
| 5,522,854 A * | 6/1996 | Ideker et al. ................... 607/6 |
| 5,540,730 A | 7/1996 | Terry, Jr. et al. | |
| 5,571,150 A | 11/1996 | Wernicke et al. | |
| 5,707,400 A | 1/1998 | Terry, Jr. et al. | |
| 5,978,702 A * | 11/1999 | Ward et al. | |
| 6,253,109 B1 | 6/2001 | Glelen | |
| 6,319,241 B1 | 11/2001 | King et al. | |
| 6,337,997 B1 | 1/2002 | Rise | |
| 6,356,784 B1 | 3/2002 | Lozano et al. | |
| 6,366,813 B1 | 4/2002 | DiLorenzo | |
| 6,459,936 B2 | 10/2002 | Fischell et al. | |
| 6,480,743 B1 | 11/2002 | Kirkpatrick et al. | |
| 6,484,059 B2 | 11/2002 | Glelen | |
| 6,526,318 B1 | 2/2003 | Ansarinia | |
| 6,609,025 B2 | 8/2003 | Barrett et al. | |
| 6,832,114 B1 * | 12/2004 | Whitehurst et al. ........... 607/40 |
| 2002/0055761 A1 * | 5/2002 | Mann et al. .................... 607/41 |
| 2002/0064501 A1 * | 5/2002 | Khan et al. ................... 424/9.2 |
| 2002/0177882 A1 | 11/2002 | DiLorenzo | |
| 2002/0188336 A1 * | 12/2002 | Bothe Loncar et al. ........ 607/96 |
| 2003/0018367 A1 | 1/2003 | DiLorenzo | |
| 2003/0144709 A1 | 7/2003 | Zabara et al. | |
| 2005/0065574 A1 * | 3/2005 | Rezai ........................... 607/45 |
| 2006/0224189 A1 * | 10/2006 | Schuler et al. .................. 607/2 |

* cited by examiner

*Primary Examiner*—George R Evanisko
*Assistant Examiner*—Michael Kahelin
(74) *Attorney, Agent, or Firm*—Bret E. Field; Bozicevic, Field & Francis, LLP

(57) ABSTRACT

Methods are provided for treating a subject for a fertility condition. In accordance with the subject methods, at least a portion of a subject's autonomic nervous system is modulated to increase the sympathetic activity/parasympathetic activity ratio in a manner that is effective to treat the subject for the condition. Embodiments of the subject invention include modulating a subject's autonomic nervous system using electrical energy and/or one or more pharmacological agents. The subject methods find use in the treatment of a variety of different fertility conditions. Also provided are kits for use in practicing the subject methods.

36 Claims, No Drawings

TREATMENT OF FEMALE FERTILITY CONDITIONS THROUGH MODULATION OF THE AUTONOMIC NERVOUS SYSTEM

FIELD OF THE INVENTION

The field of this invention is the treatment of female fertility conditions associated with the autonomic nervous system.

BACKGROUND OF THE INVENTION

Fertility conditions affect millions of female's each year. According to the National Center for Health Statistics, approximately 6.1 million women between the ages of 15-44 have impaired ability to have children (data for U.S. in 1995). While in general all of these such conditions adversely affect a woman's fertility, they in fact are a heterogeneous group of conditions such as infertility, subfertility, early pregnancy loss, spontaneous abortion, and the like.

A variety of different treatment strategies have been developed over the years in attempts to address female fertility conditions, including hormonal therapy, in vitro fertilization, artificial fertilization, embryo transfer, etc. However, despite these treatment strategies, disorders of impaired fertility remain a major clinical problem.

As such, there continues to be an interest in the development of new protocol options for treating fertility conditions.

SUMMARY OF THE INVENTION

Methods are provided for treating a subject for a fertility condition. In accordance with the subject methods, at least a portion of a subject's autonomic nervous system is modulated to increase the sympathetic activity/parasympathetic activity ratio in a manner that is effective to treat the subject for the condition. Embodiments of the subject invention include modulating a subject's autonomic nervous system using electrical energy and/or one or more pharmacological agents. The subject methods find use in the treatment of a variety of different fertility conditions. Also provided are kits for use in practicing the subject methods.

DETAILED DESCRIPTION OF THE INVENTION

Methods are provided for treating a subject for a fertility condition. In accordance with the subject methods, at least a portion of a subject's autonomic nervous system is modulated to increase the sympathetic activity/parasympathetic activity ratio in a manner that is effective to treat the subject for the condition. Embodiments of the subject invention include modulating a subject's autonomic nervous system using electrical energy and/or one or more pharmacological agents. The subject methods find use in the treatment of a variety of different fertility conditions. Also provided are kits for use in practicing the subject methods.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

As summarized above, the subject invention provides methods for treating a subject for a fertility condition by modulating at least a portion of the subject's autonomic nervous system. In further describing the subject invention, representative embodiments of the subject methods are described first in greater detail, followed by a review of various representative applications in which the subject methods may find use. Next, a review of kits for use in the subject methods is provided.

Methods

As noted above, the subject methods are methods for treating a subject for a fertility condition. More specifically, embodiments of the subject methods include treating a female subject for a fertility condition by modulating at least a portion of the subject's autonomic nervous system to increase the sympathetic activity/parasympathetic activity ratio. By "fertility condition" is meant broadly to include conditions, including disease conditions, that affect or impair the fertility of a female. Such conditions include, but are not limited to, infertility, subfertility, early pregnancy loss, spontaneous abortion, implantation failure, amenorrhea, luteal insufficiency (also referred to as luteal phase defect ("LPD")), dysmenorrhea (also referred to as pelvic pain, menstrual cramps and the like), chemical pregnancy loss, stillbirth, habitual abortion, endometriosis, and the like.

Modulation of a subject's autonomic nervous system may include increasing one or more aspects of autonomic nervous system activity in a portion of the autonomic nervous system and/or decreasing one or more aspects of autonomic nervous system activity in a portion of the autonomic nervous system. By "modulating at least a portion of a subject's autonomic nervous system" and analogous terms is meant altering or changing at least a portion of a subject's autonomic nervous system by suitable means to provide a change, alteration or shift in at least one component or aspect of the autonomic nervous system to increase the sympathetic activity/parasympathetic activity ratio. The modulation of the autonomic nervous system may affect central motor output and/or nerve conduction and/or transmitter release and/or synaptic transmission and/or receptor activation, but in any event is a change that provides an increase in the sympathetic activity/parasympathetic activity ratio (as used herein "activity" and "function" are used interchangeably).

Embodiments of the subject methods may be employed to alter the dominance of the sympathetic and parasympathetic systems and/or may be employed to modulate the differential between the two systems. Modulation of the autonomic nervous system may be accomplished by increasing and/or decreasing activity in a portion of the autonomic nervous system. By "increasing activity" and analogous terms is meant the activity in at least a portion of the autonomic nervous system may be increased, relative to the activity level prior to employing the subject methods, to modulate at least a portion of the autonomic nervous system. For example, activity in any portion of the one or more nerve fibers of the parasympathetic nervous system and/or sympathetic nervous system may be increased or "up-regulated" to provide the desired ratio of sympathetic activity/parasympathetic activity. By "decreasing activity" and analogous terms is meant that activity in at least a portion of autonomic nervous system is decreased or inhibited, relative to its activity level prior to employing the subject methods, to modulate at least a portion of the autonomic nervous system. By "decreased" or "inhibited" activity (used herein interchangeably) is meant to include, but is not limited to, disruption, down-regulating, dampening and partial and complete blockage of function or nerve impulses in at least a portion of the autonomic nervous system. For example, activity in any portion of the one or more nerve fibers of the parasympathetic nervous system and/or sympathetic nervous system may be decreased or "down-regulated" to provide the desired ratio of sympathetic activity/parasympathetic activity.

Embodiments of the subject invention include pharmacologically modulating at least a portion of a subject's autonomic nervous system to increase the sympathetic activity/parasympathetic activity ratio in at least a portion of the autonomic nervous system. Accordingly, embodiments of the subject invention may include pharmacologically increasing or decreasing sympathetic activity in at least a portion of the autonomic nervous system and/or pharmacologically increasing or decreasing parasympathetic activity in at least a portion of the autonomic nervous system. In other words, modulating at least a portion of autonomic nervous system to treat a fertility condition may be achieved by administering an effective amount of at least one pharmacological agent, e.g., an amount sufficient treat the condition of issue.

Further embodiments of the subject invention include electrically modulating at least a portion of a subject's autonomic nervous system to increase the sympathetic activity/parasympathetic activity ratio in a portion of the autonomic nervous system using electrical energy. Accordingly, embodiments of the subject invention may include electrically increasing or decreasing sympathetic activity in at least a portion of the autonomic nervous system and/or electrically increasing or decreasing parasympathetic activity in at least a portion of the autonomic nervous system. Embodiments may include electrically ablating one or more nerve fibers. In other words, modulating at least a portion of autonomic nervous system to treat a fertility condition may be achieved by administering electrical energy to at least a portion of the autonomic nervous system in an amount sufficient to treat the condition of issue.

Accordingly, embodiments of the subject invention include modulating at least a portion of a subject's autonomic nervous system to achieve a desired sympathetic activity/parasympathetic activity ratio, e.g., a ratio analogous to an average sympathetic activity/parasympathetic activity ratio observed in a healthy female of child bearing age (e.g., of like age as the treated subject) not experiencing a fertility condition. In other words, a sympathetic activity/parasympathetic activity ratio observed in a healthy, "like" or rather analogous subject (i.e., a subject not experiencing an abnormality in the autonomic nervous system), e.g., a healthy human subject of child-bearing age. As such, an average sympathetic activity/parasympathetic activity ratio observed in a healthy female of child bearing age may be referred to as an average "normal" ratio, whereas deviation from this average normal ratio to a degree that causes or at least exacerbates a fertility condition may be referred to as an "abnormal" ratio (analogous descriptors may be used to refer to individual activity levels of the sympathetic nervous system and of the parasympathetic nervous system). As the sympathetic activity/parasympathetic activity ratio varies during different phases of a female's menstrual cycle, a desired sympathetic activity/parasympathetic activity ratio is one that is commensurate with the particular menstrual cycle phase or phases being targeted, i.e., commensurate with the particular menstrual phase(s) during which modulation of at least a portion of the autonomic nervous system is desired and/or the particular menstrual cycle observed to have autonomic imbalance or rather a sympathetic function/parasympathetic function ratio that does not promote or support fertility or gestation, e.g., an abnormal sympathetic function/parasympathetic function ratio for a given particular menstrual cycle phase.

For example, the inventors of the subject invention have discovered that many fertility conditions are caused or at least exacerbated by autonomic dysfunction during one or more phases of a female's menstrual cycle, e.g., an autonomic nervous system imbalance during the luteal phase. Specifically, the inventors have discovered that an inadequate shift to a suitable sympathetic bias (i.e., an inadequate shift to sympathetic dominance) during the luteal phase and/or early gestation at least contributes to impaired female fertility in many instances. For example, while not being limited to any particular theory or hypothesis, an inadequate shift to sympathetic bias during the luteal phase may preclude the proper transition to a more fertility-favorable immune and physiologic state of a female for accepting and nurturing a successful implantation. Sympathetic bias also promotes a shift to relative T helper (Th)-2 biased immunity which may favor maternal tolerance of an embryo by attenuating Th-1 mediated interference of implantation. Sympathetic bias may further support gestation through physiological effects such as increased cardiac output and systemic vascular resistance. In such instances where an inadequate shift to sympathetic bias has occurred, the autonomic nervous system may be modulated in accordance with the subject invention in a manner to achieve a sympathetic activity/parasympathetic activity ratio analogous to that observed in a healthy, like female, e.g., analogous to an adequate shift to sympathetic bias during the luteal phase of a normal female or rather a female not experiencing an inadequate shift. As a fertility-favorable sympathetic bias promotes a shift to T helper (Th)-2 bias, the level of Th2 in a subject may be employed, e.g., to determine whether a fertility-favorable level of sympathetic activity is present in a subject. In sum, a sympathetic activity/parasympathetic activity ratio of a subject, analogous to a sympathetic activity/ parasympathetic activity ratio observed in a healthy, human female of child-bearing age during one or more particular phases of the menstrual cycle, e.g., during the luteal phase, may be provided by the subject invention.

A feature of embodiments of the subject methods is that the ratio of sympathetic activity to parasympathetic activity is increased. By "increased ratio of sympathetic activity to parasympathetic activity" and analogous terms is meant that this ratio (characterized by sympathetic activity/parasympathetic activity) is increased in at least a portion of the autonomic nervous system, where the increase is at least great enough to provide the desired results, e.g., great enough to treat a given female fertility condition. For example, in certain embodiments a subject may have an abnormal (relative to a healthy, like subject not affected by a fertility condition or the underlying cause thereof) ratio of sympathetic/parasympathetic activity and the subject invention may be employed to adjust this ratio.

While the ratio of sympathetic function/parasympathetic function may be increased according to embodiments of the subject invention, the net result may be a sympathetic bias (i.e., sympathetic dominance), parasympathetic bias (i.e., parasympathetic dominance) or the activities of the sympathetic system and parasympathetic system may be substantially equal (i.e., neither is dominant). By "bias" is meant that the particular "biased" component of the autonomic nervous system has a higher activity level than the other component. For example, a sympathetic bias refers to a higher level of sympathetic activity than parasympathetic activity, and vice versa, where such bias may be systemic or localized. The net result of the subject methods to treat a fertility condition may be higher or greater sympathetic activity relative to parasympathetic activity in at least the area of the autonomic system targeted or rather in need of modulation, higher or greater parasympathetic activity relative to sympathetic activity in at least the area of the autonomic system targeted or rather in need of modulation, or substantially equal activity levels of sympathetic activity and parasympathetic activity.

As the subject methods include modulating at least a portion of a subject's autonomic nervous system, the modulation may be systemic or regional (i.e., localized). In other words, the entire autonomic nervous system may be modulated (e.g., the entire sympathetic nervous system and/or parasympathetic nervous system may be modulated) or only a portion of the autonomic nervous system may be modulated (e.g., only a portion of the sympathetic nervous system and/or parasympathetic nervous system may be modulated). Localization may be with respect to a particular area or even to a particular nerve fiber. For example, localization may be with respect to innervations of the female reproductive organs. Localization may be with respect to the sacral roots or nerves (i.e., one or more of the five pairs of spinal nerves emerging from the sacral region of the spinal cord), pelvic nerves, spinal cord, and the like.

Embodiments of the subject methods also include determining and/or monitoring one or more indicators, effects or results of the autonomic nervous system. For example, the level of T helper cells (Th1 and/or Th2) may be monitored, e.g., as an indicator of a suitable fertility-favorable sympathetic activity/parasympathetic activity ratio. Such may be monitored at any suitable time including before, during and after modulating the autonomic nervous system in accordance with the subject invention.

Before further describing the subject methods, various aspects of the autonomic nervous system are reviewed to provide a proper foundation for the subject invention.

Review of the Autonomic Nervous System

The nervous system is divided into the somatic nervous system and the autonomic nervous system ("ANS"). In general, the somatic nervous system controls organs under voluntary control (e.g., skeletal muscles) and the ANS controls individual organ function and homeostasis. For the most part, the ANS is not subject to voluntary control. The ANS is also commonly referred to as the visceral or automatic system.

The ANS can be viewed as a "real-time" regulator of physiological functions which extracts features from the environment and, based on that information, allocates an organisms' internal resources to perform physiological functions for the benefit of the organism, e.g., responds to environment conditions in a manner that is advantageous to the organism.

The ANS conveys sensory impulses to and from the central nervous system to various structures of the body such as organs and blood vessels, in addition to conveying sensory impulses through reflex arcs. For example, the ANS controls constriction and dilatation of blood vessels; heart rate; the force of contraction of the heart; contraction and relaxation of smooth muscle in various organs; lungs; stomach; colon; bladder; visual accommodation, secretions from exocrine and endocrine glands, etc. The ANS does this through a series of nerve fibers and more specifically through efferent and afferent nerves. The ANS acts through a balance of its two components: the sympathetic nervous system and parasympathetic nervous system, which are two anatomically and functionally distinct systems. Both of these systems include myelinated preganglionic fibers which make synaptic connections with unmyelinated postganglionic fibers, and it is these fibers which then innervate the effector structure. These synapses usually occur in clusters called ganglia. Most organs are innervated by fibers from both divisions of the ANS, and the influence is usually opposing (e.g., the vagus nerve slows the heart, while the sympathetic nerves increase its rate and contractility), although it may be parallel (e.g., as in the case of the salivary glands). Each of these is briefly reviewed below.

The Parasympathetic System

The parasympathetic nervous system is the part of the autonomic nervous system controlling a variety of autonomic functions including, but not limited to, involuntary muscular movement of blood vessels and gut and glandular secretions from eye, salivary glands, bladder, rectum and genital organs. The vagus nerve is part of the parasympathetic system. Parasympathetic nerve fibers are contained within the last five cranial nerves and the last three spinal nerves and terminate at parasympathetic ganglia near or in the organ they supply. The actions of the parasympathetic system are broadly antagonistic to those of the sympathetic system, lowering blood pressure, slowing heartbeat, stimulating the process of digestion etc. The chief neurotransmitter in the parasympathetic system is acetylcholine.

More specifically, neurons of the parasympathetic nervous system emerge from the brainstem as part of the Cranial nerves III, VII, IX and X (vagus nerve) and also from the sacral region of the spinal cord via Sacral nerves 2, 3 and 4. Because of these origins the parasympathetic nervous system is often referred to as the 'craniosacral outflow'.

In the parasympathetic nervous system both pre- and postganglionic neurons are cholinergic (i.e., they utilize the neurotransmitter acetylcholine) Unlike adrenaline and noradrenaline, which the body takes around 90 minutes to metabolize, acetylcholine is rapidly broken down after release by the enzyme cholinesterase. As a result the effects are relatively brief in comparison to the sympathetic nervous system.

Each preganglionic parasympathetic neuron synapses with just a few postganglionic neurons, which are located near—or in—the effector organ, a muscle or gland. As noted above, the primary neurotransmitter in the parasympathetic system is acetylcholine ("Ach") such that ACh is the neurotransmitter at all the pre- and many of the postganglionic neurons of the parasympathetic system. However, some of the postganglionic neurons release nitric oxide as their neurotransmitter.

The Sympathetic System

The sympathetic nervous system is the part of the autonomic nervous system comprising nerve fibers that leave the spinal cord in the thoracic and lumbar regions and supply viscera and blood vessels by way of a chain of sympathetic ganglia running on each side of the spinal column which communicate with the central nervous system via a branch to a corresponding spinal nerve. The sympathetic nervous system controls a variety of autonomic functions including, but not limited to, control of movement and secretions from viscera and monitoring their physiological state, stimulation of the sympathetic system inducing e.g. the contraction of gut sphincters, heart muscle and the muscle of artery walls, and the relaxation of gut smooth muscle and the circular muscles of the iris. The chief neurotransmitter in the sympathetic system is adrenaline which is liberated in the heart, visceral muscle, glands and internal vessels, with acetylcholine acting as a neurotransmitter at ganglionic synapses and at sympathetic terminals in skin and skeletal muscle blood vessels. The actions of the sympathetic system tend to be antagonistic to those of the parasympathetic system.

More specifically, the preganglionic motor neurons of the sympathetic system arise in the spinal cord. They pass into sympathetic ganglia which are organized into two chains that run parallel to and on either side of the spinal cord. The neurotransmitter of the preganglionic sympathetic neurons is acetylcholine ("Ach") which stimulates action potentials in the postganglionic neurons.

The neurotransmitter released by the postganglionic neurons is nonadrenaline (also called norepinephrine). The action of noradrenaline on a particular structure such as a gland or muscle is excitatory is some cases, inhibitory in others. At excitatory terminals, ATP may be released along with noradrenaline.

Activation of the sympathetic system may be characterized as general because a single preganglionic neuron usually synapses with many postganglionic neurons and the release of adrenaline from the adrenal medulla into the blood ensures that all the cells of the body will be exposed to sympathetic stimulation even if no postganglionic neurons reach them directly.

Methods of Treating a Subject for a Fertility Condition by Increasing the Sympathetic Activity/Parasympathetic Activity Ratio As indicated above, the subject invention provides methods of treating a subject for a fertility condition by modulating at least a portion of the autonomic nervous system to increase the sympathetic activity/parasympathetic activity ratio in a manner effective to treat the fertility condition at issue. Any area of the autonomic nervous system (any nerve of the autonomic nerve system) may be targeted according to the subject invention. Specific area(s) of the autonomic nervous system that may be modulated will vary, and include, but are not limited to, pre- and post ganglionic nerve fibers, ganglionic structures, efferent and afferent nerve fibers, the hypothalamus, receptors on the hypothalamus, afferent autonomic nerves (sympathetic and parasympathetic) and hormonal receptors on the hypothalamus. In certain embodiments, a given nerve fiber or the like may be modulated with respect to sympathetic and/or parasympathetic activity in more than one area of the nerve fiber. The subject invention may be employed to target at least a portion of the sympathetic pathway, i.e., one or more nerves traveling from the T10 to L2 segments to the inferior mesenteric and superior hypogastric plexuses and to the pelvic plexus and/or at least a portion of the parasympathetic pathway, i.e., from the sacral 2, sacral 3 and sacral 4 segments via the interomediolateral columns to the pelvic plexus, or a combination of two or more of the above.

For example, as will be described in greater detail below, embodiments of the subject invention include electrical pacing and/or pharmacological modulation of the sympathetic nerves to promote sympathetic activity in one or more of the female pelvic organs (e.g., one or more of the ovary, fallopian tubes, uterus, cervix and vagina) and may occur at the spinal cord, from the T10 to L2 segments, inferior mesenteric and superior hypogastric plexuses or the pelvic plexus. Electrical and/or pharmacological modulation of at least a portion of the autonomic nervous system may also occur at the junction of the sympathetic nerves and the targeted pelvic organ. Electrical and/or pharmacological modulation may be employed to decrease parasympathetic activity to the area of the S234 (sacral 2, sacral 3, sacral 4) sacral segments via the interomediolateral columns to the pelvic plexus.

The autonomic nervous system may be modulated using any suitable technique, including, but not limited to, surgical methods (e.g., surgical isolation of an effector structure from sympathetic and/or parasympathetic innervation, i.e., surgically isolating an effector structure from one or more sympathetic and/or parasympathetic nerve fibers associated with it); ablation (permanently or reversibly ablating a nerve by employing energy delivery devices or cryotherapy); cryoablation; thermoablation; microwave energy; focus ultrasound; magnetic fields including internal and external magnetic fields; laser energy; optical energy; radiofrequency energy; pacing mechanisms (e.g., implantable electrode-based pacing systems, external magnetic-based pacing system, and the like); transcutaneous electrical nerve stimulation ("TENS") or transmagentic stimulation ("TMS") (see for example George, M. Stimulating the Brain. Sci Amer 2003 Sept.); pharmacological modulation and electrical modulation. Exemplary methods using pharmacological methods and electrical energy methods are now described in greater detail, where such is in no way intended to limit the scope of the invention as it is to be understood that modulation of the autonomic nervous system may be achieved using any suitable method.

Pharmacological Modulation of at Least a Portion of the Autonomic Nervous System As described above, embodiments include treating a subject for a fertility condition by pharmacologically modulating at least a portion of the subject's autonomic nervous system to increase the sympathetic activity/parasympathetic activity ratio or increase sympathetic activity relative to sympathetic activity. By "pharmacologically modulating at least a portion of a subject's autonomic nervous system" is meant altering or changing at least a portion of an autonomic nervous system by pharmacological means (i.e., administering a pharmaceutical agent to a subject) to provide a change, alteration or shift in at least one component or aspect of the autonomic nervous system. The pharmacological modulation of the autonomic nervous system may affect central motor output and/or nerve conduction and/or transmitter release and/or synaptic transmission and/or receptor activation, but in any event is a change that provides an increase in the sympathetic activity/parasympathetic activity ratio.

For example, embodiments include pharmacologically modulating at least a portion of a subject's autonomic nervous system to alter, shift or change the activity in at least one of the sympathetic system and parasympathetic system from a first state to a second state, where the second state is characterized at least by an increase in the sympathetic activity/parasympathetic activity ratio relative to the first state. One or more pharmacological agents may be employed to increase and/or decrease activity in at least a portion of the autonomic nervous system. For example, embodiments may include administering one or more pharmacological agents to achieve one or more of the following (but in any event to achieve a net result of an increase in sympathetic activity/parasympathetic activity ratio, relative to the sympathetic activity/parasympathetic activity ratio prior to pharmacological modulation): (1) increasing activity in at least one sympathetic nerve fiber to achieve an increase in activity at least a portion of the sympathetic system, (2) increasing activity in at least one parasympathetic nerve fiber to achieve an increase in activity in at least a portion of the parasympathetic system, (3) inhibiting activity in at least one sympathetic nerve fiber to achieve a decease in activity at least a portion of the sympathetic system, and (4) inhibiting activity in at least one parasympathetic nerve fiber to achieve a decease in activity in at least a portion of the parasympathetic system. Certain embodiments of the subject invention may include administering an effective amount of one or more pharmacological agents to both increase activity in at least a portion of the autonomic nervous system, e.g., increase activity in at least one sympathetic nerve fiber, and inhibit activity in at least a portion of the autonomic nervous system, e.g., inhibit activity in at least one parasympathetic nerve fiber, to treat a fertility condition.

Pharmacological modulation in accordance with the subject invention may be performed prior to and/or at the same time and/or subsequent to any other medical or clinical treatment regime such as any one or more of those described above, for example, electrical modulation of at least a portion of the subject's autonomic nervous system, e.g., as described in copending U.S. patent application Ser. No. 10/661,368, entitled "Treatment of Conditions Through Electrical Modulation of the Autonomic Nervous System", the disclosure of which is herein incorporated by reference, and the like. In other words, the subject methods may include other concomitant therapies or treatments to treat the same fertility condition.

According to embodiments of the subject invention, pharmacological modulation is accomplished by at least administering an effective amount of at least one pharmacological agent to a subject to treat the subject for a fertility condition caused, precipitated or otherwise exacerbated, influenced or affected by the ratio of the sympathetic activity/parasympathetic activity ratio. In other words, activity in at least a portion of the autonomic nervous system is at a level that is at least contributing to or otherwise affecting or exacerbating a fertility condition such a disease condition in need of treatment, and as such modulation of the autonomic nervous system may be employed to treat the condition.

That is, embodiments of the subject methods include administering an effective amount, i.e., a therapeutically effective amount, of one or more pharmacological agents to a subject to modulate at least a portion of the subject's autonomic nervous system. By "effective amount" is meant a dosage sufficient to modulate at least a portion of a subject's autonomic nervous system for a given period of time. The effective amount will vary with the age and physical condition of the subject, type and severity of the condition being treated, the duration of the treatment, the nature of any concurrent treatment, the pharmaceutically acceptable carrier used if any, and analogous factors within the knowledge and expertise of those skilled in the art. Introduction of an effective amount of a pharmacological agent to a subject resulting in a modulation of at least a portion of the autonomic nervous system that may be temporary or permanent.

Accordingly, embodiments of the subject invention include administering an effective amount of at least one pharmacological agent to a subject to treat a problem affecting fertility. In certain embodiments, more than one type of pharmacological agent may be administered at the same or different time as another pharmacological agent to treat a female for the same or different fertility condition.

The effective amount of a given pharmacological agent may vary somewhat from subject to subject, and may depend upon factors such as, but not limited to, the age and condition of the subject, the form of the pharmacological agent, the route and method of delivery, etc., as noted above. Such dosages may be determined in accordance with routine pharmacological procedures known to those skilled in the art. Pharmacological agent and/or adjuvants may be administered to a subject in a single oral dose, one time a day or more for days, weeks, months, years, even as long as a subject's lifetime or as long as the subject is of child-bearing years or as long as the subject desires fertility. For example, embodiment may include administering a given pharmacological agent one time a day over a prolonged period of time, e.g., over a particular time period coinciding with at least a portion of one or more menstrual cycle phases (e.g., the luteal phase or at least the start of the luteal phase), e.g., over about 1 week, e.g., over about 1-3 months, e.g., about 3 months to about 3 years or more, e.g., orally or with a medical infusion pump or similar device designed for delivery of a substance over a prolonged period. The frequency of administration of a pharmacological agent may vary depending, e.g., on one or more of the factors described above. For example, the frequency of administration may range from about 1 time per day to multiple times per day, e.g., about 2 times or more per day or as necessary to treat or otherwise control or manage a fertility condition. The duration of therapy depends on the type of fertility condition being treated and may range from as short as about 24 hours to as long as the child-bearing years of the subject or even as long as the life of the subject. By "adjuvants" is meant a compound that, when used in combination with the one or more pharmacological agent compounds and/or compositions, augments or otherwise alters or modifies the resultant pharmacological and/or physiological responses.

Embodiments may include daily discrete or continuous unit doses wherein the total number of daily units may be equal to the total number of days of a given predetermined phase of the menstrual cycle, the total number of days of a month or menstrual cycle, and the like, in the form of a pack. For example, embodiments may include daily discrete or continuous unit doses wherein the total number of daily units may be equal to the total number of days of a month or menstrual cycle, in the form of a monthly pack. Such a monthly pack may include daily units of the same or different dosages, e.g., the doses of certain unit doses to be administered to a subject during one or more predetermined phases of the menstrual cycle (e.g., the luteal phase) may differ in dosage from one or more other daily units to be administered to the subject during one or more other predetermined phases of the menstrual cycle.

Depending on the particular pharmacological agent administered to a subject, the pharmacological agent may be administered to a subject using any convenient means capable of resulting in the desired modulation of the autonomic nervous system. Thus, the at least one pharmacological agent may be incorporated into a variety of formulations for therapeutic administration. More particularly, the pharmacological agent may be formulated into pharmaceutical compositions by combination with appropriate, pharmaceutically acceptable carriers. By "pharmaceutically acceptable carrier" is meant a component such as a carrier, diluent, excipient, and the like of a composition that is compatible with the particular pharmacological agent and other optional ingredients of the subject pharmacological agent compositions in that a pharmaceutically acceptable carrier may be combined with the pharmacological agent without eliminating the biological or therapeutically effective activity of the pharmacological agent, and is suitable for use in subjects as provided herein without undue adverse side effects (such as toxicity, irritation, allergic response, and death). Side effects are "undue" when their risk outweighs the benefit provided by the pharmacological agent. Non-limiting examples of pharmaceutically acceptable components include, but are not limited to, any of the standard pharmaceutical carriers such as phosphate buffered saline solutions, water, emulsions such as oil/water emulsions or water/oil emulsions, microemulsions, and various types of wetting agents. Accordingly, the pharmacological agent employed in the subject methods may be formulated into preparations in solid, semi-solid (e.g., gel), liquid or gaseous forms, such as tablets, capsules, powders, granules, ointments, solutions, suppositories, injections, inhalants and aerosols. As such, administration of a pharmacological agent may be achieved in various ways, including, but not limited to, oral, buccal (e.g. sub-lingual), rectal, topical (including both skin and mucosal surfaces, including airway surfaces), parenteral (e.g., subcutaneous, intramuscular, intradermal, intravenous and intrathecal), intraperiactivityal, transdermal, intracheal, intravaginal, endocervical, intrathecal, intranasal, intravesicular, in or on the eye, in the ear canal, etc., administration. In certain embodiments, a given pharmacological agent may be administered via a transdermal patch or film system such as or analogous to that described, e.g., in U.S. Pat. Nos. 6,503,532; 5,302,395; 5,262,165; 5,248,501; 5,232,702; 5,230,896; 5,227,169; 5,212,199; 5,202,125; 5,173,302; 5,154,922; 5,139,786; 5,122,383; 5,023,252; 4,978,532; 5,324,521; 5,306,503; 5,302,395; 5,296,230; 5,286,491; 5,252,334; 5,248,501; 5,230,896; 5,227,169; 5,212,199; 5,202,125; 5,173,302; 5,171,576; 5,139,786; 5,133,972; 5,122,383; 5,120,546; 5,118,509; 5,077,054; 5,066,494; 5,049,387; 5,028,435; 5,023,252; 5,000,956; 4,911,916; 4,898,734; 4,883,669; 4,882,377; 4,840,796; 4,818,540; 4,814,173; 4,806,341; 4,789,547; 4,786,277; 4,702,732; 4,690,683; 4,627,429; and 4,585,452, the disclosures of which are herein incorporated by reference.

As noted above, embodiments may include pharmaceutical formulations for oral administration that may be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use may be obtained through combination of at least one pharmacological agent with a solid excipient, optionally grinding a resulting mixture, and processing the mixture of granules, after adding suitable additional compounds, if desired, to obtain tablets or dragee cores. Suitable solid excipients include, but are not limited to, carbohydrate or protein fillers and include, but are not limited to sugars, including lactose, sucrose, mannitol, or sorbitol; starch from corn, wheat, rice, potato, or other plants; cellulose such as methyl cellulose, hydroxypropylmethyl-cellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate; with optional lubricants, such as talc or magnesium stearate; and if desired, with diluents, buffering agents, moistening agents, preservatives and flavoring agents.

Accordingly, pharmacological formulations suitable for oral administration in accordance with the subject invention may be present in discrete units, such as capsules, cachets, lozenges, tablets, and the like, each containing a predetermined amount of the active pharmacological agent; as a powder or granules; as a solution or a suspension in an pharmacological formulations may be prepared by any suitable method of pharmacy which includes, but is not limited to, bringing into association the active pharmacological agent and a suitable carrier (which may contain one or more optional ingredients as noted above). For example, pharmacological formulations for use with the subject invention may be prepared by uniformly and intimately admixing the active pharmacological agent with a liquid or finely divided solid carrier, or both, and then, if necessary, shaping the resulting mixture. For example, a tablet may be prepared by compressing or molding a powder or granules containing the active pharmacological agent, optionally with one or more accessory ingredients. Compressed tablets may be prepared by compressing, in a suitable machine, the pharmacological agent in a free-flowing form, such as a powder or granules optionally mixed with a binder, lubricant, inert diluent, and/or surface active/dispersing agent(s). Molded tablets may be made by molding, in a suitable machine, the powdered pharmacological agent moistened with an inert liquid binder.

A pharmacological agent of this invention may also be administered in the form of suppositories for rectal administration of the drug. These formulations may be prepared by mixing a pharmacological agent with a suitable non-irritating vehicle or excipient which is solid at ordinary temperatures but liquid at the rectal temperatures and will therefore melt in the rectum to release the drug. Such materials include, but are not limited to, cocoa butter, carbowaxes and polyethylene glycols. Embodiments include a pharmacological agent made into suppositories by mixing with a variety of bases such as emulsifying bases or water-soluble bases.

A pharmacological agent of this invention may also be administered by intranasal, intraocular, intravaginal, and intrarectal routes including suppositories, insufflation, powders and aerosol formulations (for examples of steroid inhalants, see Rohatagi, *J Clin. Pharmacol.* 35:1187-1193, 1995; Tjwa, *Ann. Allergy Asthma Immunol.* 75:107-111, 1995).

For example, embodiments may also include a pharmacological agent in an aerosolized, atomized or nebulized vapor form, e.g., administrable via a metered dose device or nebulizer, and the like such that embodiments also include aerosolizing, vaporing or nebulizing one or more pharmacological agents for administration to a subject. Accordingly, a pharmacological agent may be utilized in aerosol formulation or an analogous formulation to be administered via inhalation or analogous means. The pharmacological agent employed in the practice of the present invention may be formulated into pressurized acceptable propellants such as dichlorodifluoromethane, propane, nitrogen and the like.

A pharmacological agent of the invention may be delivered transdermally, by a topical route, formulated as applicator sticks, solutions, suspensions, emulsions, gels, creams, ointments, pastes, jellies, paints, powders, and aerosols. For example, embodiments may include a pharmacological agent in the form of a discrete patch or film or plaster or the like adapted to remain in intimate contact with the epidermis of the recipient for a period of time. For example, such transdermal patches may include a base or matrix layer, e.g., polymeric layer, in which one or more pharmacological agents are retained. The base or matrix layer may be operatively associated with a support or backing. Pharmacological formulations suitable for transdermal administration may also be delivered by iontophoresis and may take the form of an optionally buffered aqueous solution of the pharmacological compound. Suitable formulations may include citrate or bis/tris buffer (pH 6) or ethanol/water and contain a suitable amount of active ingredient.

A pharmacological agent of the invention may also be delivered as microspheres for slow release in the body. For example, microspheres may be administered via intradermal injection of drug-containing microspheres, which slowly release subcutaneously (see Rao, *J. Biomater Sci. Polym. Ed.* 7:623-645, 1995); as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

A pharmaceutical formulation of the invention may be provided as a salt and may be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, a preparation may be a lyophilized powder that is combined with buffer prior to use.

Pharmacological formulations of the subject invention may be useful for parenteral administration, such as intravenous ("IV") administration, intramuscular ("IM"), subcutaneous ("SC" or "SQ"), mucosal. The formulations for administration may include a solution of the pharmacological agent dissolved in a pharmaceutically acceptable carrier. Among the acceptable vehicles and solvents that may be employed, include, but are not limited to, water and Ringer's solution, an isotonic sodium chloride, etc. In addition, sterile fixed oils may conventionally be employed as a solvent or suspending medium. For this purpose any bland fixed oil may be employed including synthetic mono- or diglycerides. In addition, fatty acids such as oleic acid can likewise be used in the preparation of injectables. Accordingly, a pharmacological agent may be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of pharmacological agent in these formulations may vary widely, and will be selected based on fluid volumes, viscosities, body weight, and the like, in accordance with the particular mode of administration selected and the patient's needs. For IV administration, the formulation may be a sterile injectable preparation, such as a sterile injectable aqueous or oleaginous suspension. This suspension may be formulated according to the known art using those suitable dispersing or wetting agents and suspending agents. The sterile injectable preparation may also be a sterile injectable solution or suspension in a nontoxic parenterally-acceptable diluent or solvent, such as a solution of 1,3-butanediol, and the like. Accordingly, pharmacological formulations suitable for parenteral administration may include sterile aqueous and non-aqueous injection solutions of one or more active pharmacological agents, which preparations may be isotonic with the blood of the intended recipient. These preparations may contain, buffers and solutes which render the formulation isotonic with the blood of the intended recipient. Aqueous and non-aqueous sterile suspensions may include suspending agents and thickening agents. The formulations may be presented in single- or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind described above.

In other embodiments, the pharmacological formulations of the invention may be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the pharmacological agent into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). Accordingly, embodiments may include a pharmacological agent administered as liposomal formulations of the pharmacological agent. Methods for preparing liposomal suspensions are known in the art and thus will not be described herein in great detail. Briefly, in those embodiments where the pharmacological agent is an aqueous-soluble pharmacological agent, the pharmacological agent may be incorporated into lipid vesicles using conventional liposome technology. In such instances, due to the water solubility of the pharmacological agent, the pharmacological agent may be substantially entrained within the hydrophilic center or core of the liposomes. The lipid layer employed may be of any conventional composition and may either contain cholesterol or may be cholesterol-free. When the pharmacological agent of interest is water-insoluble, the pharmacological agent may be substantially entrained within the hydrophobic lipid bilayer which forms the structure of the liposome employing conventional liposome formation technology. In either instance, the liposomes which may be produced may be reduced in size, as through the use of standard sonication and homogenization techniques. Embodiments of liposomal formulations containing the pharmacological agent of interest may be lyophilized to produce a lyophilizate which may be reconstituted with a pharmaceutically acceptable carrier, such as water, to regenerate a liposomal suspension.

Embodiments of the pharmacological agent employed in the practice of the subject invention may include pharmaceutical compositions that may be prepared from water-insoluble compounds, or salts thereof, such as aqueous base emulsions. In such embodiments, the pharmacological composition will typically contain a sufficient amount of pharmaceutically acceptable emulsifying agent to emulsify the desired amount of the pharmacological agent. Useful emulsifying agents include, but are not limited to, phosphatidyl cholines, lecithin, and the like.

As noted above, in addition to active pharmacological agent, the pharmaceutical compositions of the subject invention may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Furthermore, pharmacological compositions may, though not always, contain microbial preservatives. Microbial preservatives that may be employed include, but are not limited to, methylparaben, propylparaben, and benzyl alcohol. The microbial preservative may be employed when the pharmacological formulation is placed in a vial designed for multidose use. Pharmaceutical compositions for use in practicing the subject methods may be lyophilized using techniques well known in the art.

Pharmaceutically acceptable excipients, such as vehicles, adjuvants, carriers or diluents, that may be employed in the subject invention are readily available to the public. Moreover, pharmaceutically acceptable auxiliary substances, such as pH adjusting and buffering agents, tonicity adjusting agents, stabilizers, wetting agents and the like, are readily available to the public.

Embodiments may also include administration of a pharmacological agent using a pharmacological delivery device such as, but not limited to, pumps (implantable or external devices and combinations of both (e.g., certain components are implantable and others may be external to the body such as controls for the implantable components), epidural injectors, syringes or other injection apparatus, catheter and/or reservoir operatively associated with a catheter, etc. For example, in certain embodiments a delivery device employed to deliver a given pharmacological agent to a subject may be a pump, syringe, catheter or reservoir operably associated with a connecting device such as a catheter, tubing, or the like. Containers suitable for delivery of a pharmacological agent to a pharmacological agent administration device include instruments of containment that may be used to deliver, place, attach, and/or insert the pharmacological agent into the delivery device for administration of the pharmacological agent to a subject and include, but are not limited to, vials, ampules, tubes, capsules, bottles, syringes and bags. Embodiments may also include administration of a pharmacological agent via a biodegradable implant drug delivery device. Such may be accomplished by employing syringes to deposit such a biodegradable delivery device under the skin of a subject. The implants degrade completely, so that removal is not necessary.

Embodiments may include employing an electrode to deliver a pharmacological agent to a subject. For example, an electrode may be used that has a small port at its tip which is connected to a reservoir or pump containing a pharmacological agent. The pharmacological agent delivery electrode may be implanted using any suitable technique such as surgical cut down, laproscopy, endoscopy, percutaneous procedure, and the like. In certain embodiments a reservoir or pump may also be implanted in the subject's body. The pharmacological agent delivery electrode, or other analogous device, may be controllable such that the amount of pharmacological agent delivered, the rate at which the pharmacological agent may be delivered, and the time period over which the pharmacological agent may be delivered, etc., may be controllable and may be adjusted.

In certain embodiments, one or more pharmacological agents may be included in seminal fluid used in an assisted reproductive technology such as in vitro fertilization ("IVF") and other analogous technologies (e.g., intracytoplasmic sperm injection ("ICSI"), gamete intrafallopian transfer ("GIFT"), zygote intrafallopian transfer ("ZIFT"), and the like).

In certain embodiments, the pharmaceutically acceptable carrier may be preservative free. By "preservative free" is meant the substantial absence of chemical, antibacterial, antimicrobial, or antioxidative additives, or the like, from the pharmaceutically acceptable carriers of the present invention. "Substantial absence" may mean that no preservative is present in the compositions or that trace amounts may be present that impart no detectable effect otherwise attributable to a preservative. For example, the pharmaceutically acceptable carrier may be characterized by the substantial absence of chemical, antibacterial, antimicrobial, or antioxidative additives or the like (e.g., contain less than about 5.0, 4.0, 3.0, 2.0, 1.0, 0.5, 0.1, 0.05, 0.01, or even about 0.00 percent by weight of a preservative). Further, such formulations may be substantially or essentially free of alcohols such as ethanol (e.g., contain less than about 5.0, 4.0, 3.0, 2.0, 1.0, 0.5, 0.1, 0.05, 0.01, or even about 0.00 percent by weight of alcohols such as ethanol). Examples of suitable pharmacological formulations include, but are not limited to, formulations that include one or more active pharmacological agents and physiological saline solution (optionally including other typical ingredients such as other active agents and buffers).

As noted above, in pharmaceutical dosage forms, a given pharmacological agent may be administered alone or with or in appropriate association, as well as in combination, with other pharmaceutically active compounds. As used herein, "administered with" means that a given pharmacological agent and at least one other adjuvant (including one or more other different pharmacological agents) are administered at times sufficiently close that the results observed are indistinguishable from those achieved when the pharmacological agent and at least one other adjuvant are administered at the same point in time. The pharmacological agent and at least one other adjuvant may be administered simultaneously (i.e., concurrently) or sequentially. Simultaneous administration may be carried out by mixing a given pharmacological agent and at least one other adjuvant prior to administration, or by administering a given pharmacological agent and at least one other adjuvant at the same point in time. Such administration may be at different anatomic sites or using different routes of administration. The phrases "concurrent administration," "administration in combination," "simultaneous administration" or "administered simultaneously" may also be used interchangeably and mean that a given pharmacological agent and at least one other adjuvant are administered at the same point in time or immediately following one another. In the latter case, the pharmacological agent and at least one other adjuvant are administered at times sufficiently close that the results produced are synergistic and/or are indistinguishable from those achieved when the at least one pharmacological agent and at least one other adjuvant are administered at the same point in time. Alternatively, a pharmacological agent may be administered separately from the administration of an adjuvant, which may result in a synergistic effect or a separate effect. The methods and excipients described herein are merely exemplary and are in no way limiting.

Unit dosage forms for oral or rectal administration such as syrups, elixirs, and suspensions may be provided wherein each dosage unit, for example, teaspoonful, tablespoonful, tablet or suppository, contains a predetermined amount of a pharmacological agent. Similarly, unit dosage forms for injection or intravenous or other suitable administration route may include the pharmacological agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of pharmacological agent(s) calculated in an amount sufficient to produce the desired effect in association with a pharmaceutically acceptable diluent, carrier or vehicle. The specifications for the unit dosage forms of a given pharmacological agent employed in the practice of the present invention depend on, for example, the particular pharmacological agent employed and the effect to be achieved, the pharmacodynamics associated with the particular pharmacological agent in the subject, etc.

As noted above, those of skill in the art will readily appreciate that dose levels may vary as a function of the specific pharmacological agent, the nature of the delivery vehicle, and the like. Dosages for a given pharmacological agent are readily determinable by those of skill in the art by a variety of means. Exemplary dosage levels are provided herein and are not to be construed to limit the scope of the invention in any manner.

A wide variety of different pharmacological agents may be employed in the practice of the subject methods, where the particular pharmacological agent or combination of pharmacological agents employed will depend on, e.g., the subject being treated, the condition being treated, duration of treatment, whether it is desired to increase activity in the parasympathetic system and/or increase activity in the sympathetic system and/or decrease activity in the sympathetic system and/or decrease activity in the parasympathetic system, etc. Representative pharmacological agents (and analogs and salts thereof) include, but are not limited to, one of more of the following: beta agonists, e.g., dobutamine, metaproterenol, terbutaline, ritodrine, albuterol; alpha agonists, e.g., selective alpha 1-adrenergic blocking agents such as phenylephrine, metaraminol, methoxamine; prednisone and steroids, (e.g., available under the brand names CORATN, DELTASONE, LIQUID PRED, MEDICORTEN, ORASONE, PANASOL-S, PREDNICEN-M, PREDNISONE INTENSOL); indirect agents that include norepinephrine, e.g., ephedrine, ampthetamines, phenylpropanolamines, cyclopentamines, tuaminoheptanes, naphazolines, tetrahydrozolines; epinephrine; norepinephrine; acetylcholine; sodium; calcium; angiotensin I; angiotensin II; angiotensin converting enzyme I ("ACE I"); angiotensin converting enzyme II ("ACE II"); aldosterone; potassium channel blockers and magnesium channel blockers, e.g., valproate (sodium valproate, valproic acid), lithium; cocaine; amphetamines; ephedrine; terbutaline; dopamine; doputamine; antidiuretic hormone ("ADH") (also known as vasopressin); oxytocin (including PITOCINE); THC cannabinoids; and the like; and combinations thereof.

As noted above, embodiments include administering an effective amount of a first pharmacological agent and an effective amount of at least a second, different pharmacological agent, e.g., concurrently administered, where the two may differ in one or more of a variety of aspects, e.g., dosage, type, route of administration, etc. For example, embodiments may include administering a first type of pharmacological agent and at least one other type of pharmacological agent to provide an enhanced therapeutic effect. By "enhanced therapeutic effect" is meant that at least the initial relief of the particular fertility condition being treated by the first pharmacological agent employed occurs more quickly with a combination of the first pharmacological agent and at least one other different pharmacological agent, as compared to the same doses of each component given alone, or that doses of one or all component(s) are below what would otherwise be a minimum effective dose (a "sub-MED").

Accordingly, embodiments of the subject invention includes treating a subject for a fertility condition by modulating at least a portion of the subject's autonomic nervous system by administering a first pharmacological agent together with at least one other, different pharmacological agent. The pharmacological agents may be concomitantly administered as described above, i.e., they may be given in close enough temporal proximity to allow their individual therapeutic effects to overlap. For example, embodiments of the subject invention may include the co-timely administration of a first pharmacological agent and at least a second, different pharmacological agent. By "co-timely" with respect to drug administration is meant administration of a second pharmacological agent for the treatment of a fertility condition while a first pharmacological agent is still present in a subject's system at an effective amount. It is to be understood that in some instances this will require sequential administration. Alternatively, multiple routes of administration may be employed, e.g., intravenous or subcutaneous injection of a first pharmacological agent may be combined with oral administration of a second, different pharmacological agent.

Embodiments also include pharmaceutical compositions in unit dosage forms that are useful in treating fertility conditions by modulating at least a portion of a subject's autonomic nervous system and which contain a first pharmacological agent and at least a second, different type of pharmacological agent. In other words, a single drug administration entity or unit dosage form may include two or more pharmacological agents. For example, a single tablet, capsule, dragee, trocheem suppository, syringe, transdermal patch, and the like, combining two or more pharmacological agents would be a unit dosage form. The therapeutic agents present in a unit dosage form may be present in amounts such that, upon administration of one or more unit doses of the composition, a subject may experience a longer lasting efficacy than with the administration of either agent alone. Such compositions may be included as part of a therapeutic package in which one or more unit doses are placed in a finished pharmaceutical container. Labeling may be included to provide directions for using the composition in the treatment of a condition by modulating at least a portion of a subject's autonomic nervous system. The actual amounts of each agent in such compositions will vary according to the specific compositions being utilized, the particular compositions formulated, the mode of application, the particular route of administration, and the like. Dosages for a given subject can be determined using conventional considerations, e.g., by customary comparison of the differential activities of the subject compositions and of a known agent, or by means of an appropriate, conventional pharmacological protocol. A person of ordinary skill in the art will be able without undue experimentation, having regard to that skill and this disclosure, to determine an effective amount of a particular pharmacological agent for practice of this invention. For example, embodiments may include dosages conventionally administered for the particular pharmacological agents employed, where such dosages are known in the art.

Accordingly, in practicing the subject methods, an effective amount of a pharmacological agent is administered to a subject to treat a fertility condition affecting the subject. As noted above, the particular dosage, mode of administration, treatment times, etc., will vary according to a variety of factors, but will generally fall within the ranges conventionally administered for the particular pharmacological agent employed. As noted above, the dose of pharmacological agent will be different for different subject, condition(s) treated, etc. The following descriptions of exemplary embodiments describe average doses and may vary. Such descriptions are for exemplary purposes only and are in no way intended to limit the scope of the invention. For example, the number of capsules or tablets, teaspoonfuls of solution, and the like, administered depends at least in part on the strength of the particular pharmacological agent administered. Furthermore, the number of doses administered each day, the time allowed between doses, and the length of time a subject takes the medicine, etc., depend on the condition being treated, i.e., the condition for which a subject is taking the pharmacological agent. Exemplary treatment protocols are now provided.

Beta Agonists:

As described above, embodiments may include administering an effective amount of a beta agonist to a subject to treat a fertility condition. Embodiments may include administering dosages of about 0.5 to about 1.0 micrograms/kilogram/minute of dobutamine intravenously, e.g., dosages of about 500 micrograms/ml to about 2000 micrograms/ml may be administered. Embodiments may include administering dosages of terbutaline at about 0.25 mg to about 0.5 mg intramuscularly ("IM"), e.g., not more than about 0.5 mg within a four hour period. Embodiments may include administering dosages of ritodrine at about 50 to about 350 micrograms per minute intravenously. Embodiments may include administering dosages of albuterol via nebulizer at about 0.5 ml of 0.5% inhalation solution with about 2.5 ml sterile saline solution given over about 5 to about 15 minutes three to four times per day. Embodiments may include administering dosages of metaproterenol via nebulizer every four hours wherein a vial containing 0.4% metaproterenol sulfate is equivalent to 0.2 ml of metaproterenol sulfate inhalation solution 5% diluted to 2.5 ml with normal saline.

Alpha Agonists:

As described above, embodiments may include administering an effective amount of an alpha agonist to a subject to treat a fertility condition. Embodiments may include administering dosages of phenylephrine, e.g., subcutaneously or intramuscularly: from 1 mg to about 10 mg., wherein the initial dose generally should not exceed 5 mg.; intravenously: from about 0.1 mg to about 0.5 mg., wherein generally the initial dose should not exceed 0.5 mg. Injections are typically not repeated more often than about every 10 to 15 minutes. Embodiments may include administering dosages of metaraminol subcutaneously at about 2 to about 10 mg for an interval of about 10 minutes.

Prednisone and Steroids:

As described above, embodiments may include administering an effective amount of prednisone or a steroid to a subject to treat a fertility condition. Embodiments may include administering dosages of prednisone or a steroid by mouth at about 5 to about 60 mg/day, once per day. For example, prednisone may be in the form of a solution, syrup or tablet and doses may be given once daily or every other day and about 2.5-15 mg may be taken by a subject 2-4 times daily.

Indirect Agents that Include Norepinephrine:

As described above, embodiments may include administering an effective amount of an indirect agents that include norepinephrine to a subject to treat a fertility condition. Embodiments may include administering dosages of ephedrine IM or IV at about 25 to about 50 mg once per day. Embodiments may include administering dosages of phenylpropanolamine by mouth at about 25 mg every four hours, up to about 150 mg/day. Embodiments may include administering dosages of ampthetamine by mouth at about 2.5 mg to about 60 mg once per day.

Epinephrine:

As described above, embodiments may include administering an effective amount of epinephrine to a subject to treat a fertility condition. Embodiments may include intravenously administering epinephrine at about 0.1 to about 0.25 mg (about 1 to about 2.5 ml of 1:10,000 solution) once every 20 to 30 minutes.

Norepinephrine:

As described above, embodiments may include administering an effective amount of norepinephrine to a subject to treat a fertility condition. Embodiments may include intravenously administering norepinephrine at about 0.5 to about 1.0 mg (about 5 to about 10 ml of 1:10,000 solution) once every 5 minutes.

Potassium Channel Blockers and Magnesium Channel Blockers:

As described above, embodiments may include administering an effective amount of a potassium channel blocker or a magnesium channel blocker to a subject to treat a fertility condition. Embodiments may include administering lithium by mouth at about 10 to about 60 mg/kg once per day. Embodiments may include administering valproate by mouth at about 10 to about 60 mg/kg once per day.

Acetylcholine

As described above, embodiments may include administering an effective amount of acetylcholine to a subject to treat a fertility condition. Embodiments may include administering acetylcholine in the form of eye drops at about 0.75 to about 10 milligrams/ml acetylcholine.

Cocaine:

As described above, embodiments may include administering an effective amount of cocaine to a subject to treat a fertility condition. Embodiments may include administering cocaine topically on mucus membranes, e.g., about 10% cocaine hydrochloride.

Amphetamines:

As described above, embodiments may include administering an effective amount of an amphetamine to a subject to treat a fertility condition. Embodiments may include administering an amphetamine by mouth at about 5 to about 10 mg per day, e.g., 10 mg/day in divided doses.

Ephedrine:

As described above, embodiments may include administering an effective amount of ephedrine to a subject to treat a fertility condition. Embodiments may include administering ephedrine sulfate injection at about 10 to about 50 mg injected subcutaneously or intramuscularly (equivalent to 0.2 to 1.0 ml of 5% solution).

Terbutaline:

As described above, embodiments may include administering an effective amount of terbutaline to a subject to treat a fertility condition. Embodiments may include administering terbutaline intramuscularly at about 0.25 mg, e.g., one time, and typically not more than about 0.5 mg within a 4 hour period.

Dopamine:

As described above, embodiments may include administering an effective amount of dopamine to a subject to treat a fertility condition. Embodiments may include administering dopamine intravenously at about 2 to about 50 microgram/kg/minute, wherein each milliliter of a 40 mg/ml preparation contains 40 mg of dopamine hydrochloride (equivalent to 32.31 mg of dopamine base). Embodiments may also include administering levodopa (L-dopa) in combination with carbidopa taken by mouth, e.g., about 25 mg carbidopa (up to about 2500 mg per day) and about 100 mg levodopa one half tablet, daily. Embodiments may also include administering bromocriptine (e.g., available under the brand name PARLODEL) by mouth at about 1.25 to about 100 mg per day.

Doputamine:

As described above, embodiments may include administering an effective amount of doputamine to a subject to treat a fertility condition. Embodiments may include intravenously administering doputamine at about 0.5 to about 1.0 microgram/kg/min (up to about 500 microgram/ml).

Antidiuretic Hormone ("ADH") (Also Known as Vasopressin):

As described above, embodiments may include administering an effective amount of ADH to a subject to treat a fertility condition. Embodiments may include subcutaneously or intramuscularly administering about 5 to about 10 units of AHD two or three times per day.

Oxytocin:

As described above, embodiments may include administering an effective amount of oxytocin to a subject to treat a fertility condition. Embodiments may include intravenously administering oxytocin (e.g., available under the brand name PITOCIN) at about 1 to about 2 mU/mm (solution of 1 ml (10 units) combined with 1,000 ml of a non hydrating diluent).

THC Cannabinoids:

As described above, embodiments may include administering an effective amount of THC cannibinoid to a subject to treat a fertility condition. Embodiments may include administering THC cannibinoid by rectal suppository at about 2.5 mg two times per day; or about 10 to about 20 mg one, two or three times per day by mouth; or 1 mg intravenously, e.g., one time; or about 200 mg once per day by mouth.

In certain embodiments, a given pharmacological agent may be administered at or near the time of a particular phase of a subject's menstrual cycle, i.e., in close temporal proximity to, including during, one or more phases of a subject's menstrual cycle. For example, embodiments of the subject methods may include administration of a pharmacological agent to achieve a particular sympathetic activity/parasympathetic activity ratio during at least a portion of the menses phase and/or follicular phase and/or the ovulation phase and/or the luteal phase. Of interest is the administration of a pharmacological agent at least near the time of, or during at least a portion of, the luteal phase to modulate the autonomic nervous system to increase the sympathetic activity/parasympathetic activity ratio, e.g., to provide a suitable sympathetic dominance relative to the parasympathetic system, to treat the fertility condition of interest. For example, embodiments may include administering at least one pharmacological agent to increase the sympathetic activity/parasympathetic activity ratio during the luteal phase, after ovulation. At least one pharmacological agent to increase the sympathetic activity/parasympathetic activity ratio may be administered before and/or during and/or after insemination, e.g., at least one pharmacological agent to increase the sympathetic activity/parasympathetic activity ratio may be administered prior to, during and/or after artificial insemination.

The luteal phase is the part of the cycle that starts at ovulation and ends the day before a female's next period and usually lasts between about 12 to about 16 days. As such, embodiments of the subject invention may include administering an effective amount of a pharmacological agent at least one time during ovulation and/or at least one time during the luteal phase to increase the sympathetic activity/parasympathetic activity ratio, where embodiments may include administration during about all of the days of a subject's luteal phase.

The subject methods typically include determining (e.g., predetermining) the occurrence of one or more phases of a subject's menstrual cycle by any suitable method, e.g., using hormone-specific blood tests, urine tests, etc., as is known to those of skill in the art. For example, the onset of the luteal phase may be determined using a urine leutinizing hormone ("LH") detection test or kit, as are known in the art, e.g., as available under the brand names OVUQUICK ONE-STEP, CLEARPLAN EASY and SURESTEP. Other methods of determining the onset, duration, end, etc., of a given menstrual phase may be employed and include empirical and non-empirical methods, e.g., calendar methods (counting days), estimating the start, duration and/or end of a particular menstrual cycle phase, and the like. Regardless of the particular method employed, the onset of ovulation and/or the luteal phase may be determined and one or more of the pharmacological agents described above may be administered at or near the determined start of the subject's luteal phase and/or during at least part of a subject's determined luteal phase, including all days of the subject's luteal phase.

Electrical Modulation of at Least a Portion of the Autonomic Nervous System

As described above, embodiments of the subject invention may also include electrically modulating at least a portion of the autonomic nervous system to increase the sympathetic activity/parasympathetic activity ratio. By "electrically modulating at least a portion of a subject's autonomic nervous system" is meant altering or changing at least a portion of an autonomic nervous system by applying electrical energy to provide a change, alteration or shift in at least one component or aspect of the autonomic nervous system, as will be described in greater detail below. The electrical modulation of the autonomic nervous system may affect central motor output and/or nerve conduction and/or transmitter release and/or synaptic transmission and/or receptor activation, but in any event is a change that provides an increase in the sympathetic activity/parasympathetic activity ratio.

For example, embodiments include electrically modulating at least a portion of a subject's autonomic nervous system to alter, shift or change the activity in at least one of the sympathetic system and parasympathetic system from a first state to a second state, where the second state is characterized at least by an increase in the sympathetic activity/parasympathetic activity ratio relative to the first state. Electrical energy may be employed to increase and/or decrease activity in at least a portion of the autonomic nervous system. For example, embodiments may include electrically modulating at least a portion of the autonomic nervous system to achieve one or more of the following (but in any event to achieve a net result of an increase in sympathetic activity/parasympathetic activity ratio, relative to the sympathetic activity/parasympathetic activity ratio prior to pharmacological modulation): (1) increasing activity in at least one sympathetic nerve fiber to achieve an increase in activity in at least a portion of the sympathetic system, (2) increasing activity in at least one parasympathetic nerve fiber to achieve an increase in activity in at least a portion of the parasympathetic system, (3) inhibiting activity in at least one sympathetic nerve fiber to achieve a decrease in activity in at least a portion of the sympathetic system, and (4) inhibiting activity in at least one parasympathetic nerve fiber to achieve a decrease in activity in at least a portion of the parasympathetic system. Certain embodiments of the subject invention may include electrically modulating the autonomic nervous system to both increase activity in at least a portion of the autonomic nervous system, e.g., increase activity in at least one sympathetic nerve fiber, and inhibit activity in at least a portion of the autonomic nervous system, e.g., inhibit activity in at least one parasympathetic nerve fiber, to treat a fertility condition. Accordingly, embodiments of the subject methods include providing electrical energy to at least a portion of a subject's autonomic nervous system, where such electrical energy may be excitatory or inhibitory and in certain embodiments may be both excitatory and inhibitory energies.

As noted above, electrical modulation in accordance with the subject invention may be performed prior to and/or at the same time and/or subsequent to any other medical or clinical treatment regime such as any of those described above, for example, pharmacological modulation of at least a portion of the subject's autonomic nervous system. In other words, the subject methods may include other, concomitant therapies or treatments to treat the same or different fertility condition that do not employ electrical energy.

According to embodiments of the subject invention, electrical modulation is accomplished by at least administering electrical energy to a subject in a manner sufficient to treat the subject for a fertility condition caused, precipitated or otherwise exacerbated, influenced or affected by the ratio of the sympathetic activity/parasympathetic activity ratio. In other words, activity in at least a portion of the autonomic nervous system is at a level that is at least contributing to or otherwise affecting or exacerbating a fertility condition such a disease condition in need of treatment, and as such modulation of the autonomic nervous system may be employed to treat the condition.

Methods and devices suitable for use in electrically modulating a portion of subject's autonomic nervous system, and which may be employed in the practice of the subject invention, are described in detail in copending U.S. application Ser. No. 10/661,368, entitled "Treatment of Conditions Through Electrical Modulation of the Autonomic Nervous System", the disclosure of which is herein incorporated by reference.

In general, modulating at least a portion of the autonomic nervous system using electrical energy may be accomplished with the use of an electric energy applying devices (also referred to as electrical energy supplying or delivering), such as, e.g., described in the above-noted copending application. Once an electric energy applying device is positioned in a suitable position on or about one or more targeted areas of the autonomic nervous system such as one or more parasympathetic nerve fibers and/or one or more sympathetic nerve fibers, electrical energy is applied to the area(s) (e.g., the targeted nerve fiber(s)) for a period of time sufficient to provide the desired modulation of the autonomic nervous system. This period of time will vary depending on the area (e.g., the nerve fiber) being treated, the fertility condition being treated, the particulars of the device used, etc.

As described in greater detail below, certain embodiments include simultaneously monitoring (i.e., in "real time") the parasympathetic activity and/or sympathetic activity such that electrical energy is applied until the desired increase in sympathetic activity/parasympathetic activity ratio is observed. Still further, in many embodiments once the desired ratio is achieved, electrical energy may be repeatedly applied thereto one or more times to maintain the desired state such that the subject methods may be repeated one or more times, i.e., the subject methods include chronic administration of electrical energy to at least one area of the autonomic nervous system. For example, in certain embodiments electrical energy (e.g., intermittent mild electrical pulses) may be delivered to a given area of the autonomic nervous system twenty-four hours a day for a period of days, weeks, months, or even years in certain embodiments, e.g., delivered to a given area during one or more predetermined phases of a subject's menstrual cycle such as during a predetermined luteal phase.

During the period of time that a given area of the autonomic nervous system is electrically modulated, the electrical energy may be applied substantially continuous, including continuous or intermittent (i.e., pulsed or periodic), where in many embodiments the electrical energy is in the form of electrical pulses. In other words, in certain embodiments a given area of the autonomic nervous system (e.g., a given nerve fiber) may be continuously contacted with electrical energy during the above-described period of time and in certain other embodiments a given area of the autonomic nervous system (e.g., a given nerve fiber) may be pulsed or intermittently contacted with electrical energy during the period of time described above.

In accordance with the subject methods to electrically modulate at least one area of the autonomic nervous system, once operatively positioned the electrical energy applying device is activated to provide an electrical signal to the targeted area such as to one or more nerve fiber(s) in a manner to increase the sympathetic activity/parasympathetic activity ratio at least in the particular area being contacted with electrically energy and in certain instances in adjacent areas or in the entire autonomic system, e.g., systemically in certain instances. For example, many nerve fibers are in close proximity and thus application of electrical energy to one nerve fiber may also increase or decrease activity in one or more other nerve fibers, e.g., nerve fibers in close proximity thereto.

In practicing the subject methods, activation of the electrical energy supplying device directly applies the electrical output of the device, i.e., electrical impulses, to the targeted area. For example, electrodes may be positioned to direct impulses to pelvic nerves, sacral roots, spinal cord, and the like. The exact parameters of the protocol may vary depending on the particular subject, fertility condition being treated, etc. An electronic current wave may be provided when the electrical energy is applied. In certain embodiments, the current wave includes current waves of high frequency, e.g., high frequency pulses, where the current wave may also include low frequency amplitude modulation. In certain embodiments, a plurality of high frequency bursts of current pulses may be applied in addition to the application of underlying low frequency continuous stimulus. Monopolar or multipolar technologies may be employed.

For example, to increase activity in a portion of the autonomic nervous system, voltage or intensity may range from about 1 millivolt to about 1 volt or more, e.g., 0.1 volt to about 50 volts, e.g., from about 0.2 volt to about 20 volts and the frequency may range from about 1 Hz to about 2500 Hz, e.g., about 1 Hz to about 1000 Hz, e.g., from about 2 Hz to about 100 Hz in certain embodiments. In certain embodiments a pure d-c voltages may be employed. The pulse width may range from about 1 microsecond to about 2000 microseconds or more, e.g., from about 10 microseconds to about 2000 microseconds, e.g., from about 15 microseconds to about 1000 microseconds, e.g., from about 25 microseconds to about 1000 microseconds. The electrical output may be applied for at least about 1 millisecond or more, e.g., about 1 second, e.g., about several seconds, where in certain embodiments the stimulation may be applied for as long as about 1 minute or more, e.g., about several minutes or more, e.g., about 30 minutes or more may be used in certain embodiments.

To inhibit activity or conduction in a portion of the sympathetic nervous system, voltage or intensity may range from about 1 millivolt to about 1 volt or more, e.g., 0.1 volt to about 50 volts, e.g., from about 0.2 volt to about 20 volts and the frequency may range from about 1 Hz to about 2500 Hz, e.g., about 50 Hz to about 2500 Hz. In certain embodiments a pure d-c voltages may be employed. The pulse width may range from about 1 microseconds to about 2000 microseconds or more, e.g., from about 10 microseconds to about 2000 microseconds, e.g., from about 15 microseconds to about 1000 microseconds, e.g., from about 25 microseconds to about 1000 microseconds. The electrical energy may be applied for at least about 1 millisecond or more, e.g., about 1 second, e.g., about several seconds, where in certain embodiments the electrical energy may be applied for as long as about 1 minute or more, e.g., about several minutes or more, e.g., about 30 minutes or more may be used in certain embodiments.

The time period for modulating at least a portion of a subject's autonomic nervous system using electrical energy is analogous to that described above for pharmacologically modulating at least a portion of a subject's autonomic nervous system.

A variety of different devices for applying electrical energy to stimulate or inhibit at least a portion of the autonomic nervous system in accordance with the subject invention may be employed as described in the above referenced, copending U.S. application Ser. No. 10/661,368, the disclosure of which is herein incorporated by reference. In general, devices suitable for use in practicing embodiments of the subject invention are herein referred to as electrical energy delivering devices. Such devices may be positioned directly on a targeted area, e.g., positioned below the skin of a subject directly on or adjacent a portion of the autonomic nervous system (e.g., one or more nerve fibers) such as an implantable device, or may be an external device (i.e., some or all of the device may be external to the subject). In accordance with embodiments of the subject invention, one or more electrodes or electrical contacts may be positioned directly on or adjacent a targeted area of the autonomic nervous system, i.e., directly on or adjacent a portion of the parasympathetic and/or sympathetic system, where the one or more electrodes may be surgically implanted directly on or adjacent a targeted nerve fiber of a subject. In further describing the subject invention, a single electrode is described however it is to be understood that multiple electrodes may be employed and features and characteristics of the single electrode described herein are applicable to any other electrodes that may be employed in the practice of the subject invention.

Electrical energy delivering devices that may be employed in the practice of the subject methods typically includes a stimulator (or inhibitor) such as an electrode, a controller or programmer and one or more connectors for connecting the stimulating device to the controller. In certain embodiments more than one electrode may be employed. In further describing representative electrodes, such are described in the singular, but it will be apparent that more than one electrode may be used, where such may be the same or may be different in one or more aspects. Accordingly, the description of a representative electrode suitable for use in the subject methods is applicable to other electrodes that may be employed.

The electrode employed in the subject invention is typically controllable to provide output signals that may be varied in voltage, frequency, pulse width, current and intensity. The electrode is typically one that provides both positive and negative current flow from the electrode and/or is capable of stopping current flow from the electrode and/or changing the direction of current flow from the electrode. For example, embodiments include an electrode that is controllable in these respects, i.e., controllable in regards to producing positive and negative current flow from the electrode, stop current flow from the electrode, change direction of current flow from the electrode, and the like. In certain embodiments, the electrode has the capacity for variable output, linear output and short pulse width.

The energy source for the electrical output is provided by a battery or generator such as a pulse generator that is operatively connected to the electrode. The energy source may be positioned in any suitable location such as adjacent to the electrode (e.g., implanted adjacent the electrode), or a remote site in or on the subject's body or away from the subject's body in a remote location and the electrode may then be connected to the remotely positioned energy source using wires, e.g., may be implanted at a site remote from the electrode or positioned outside the subject's body in certain instances. Of interest are implantable generators analogous to a cardiac pacemaker.

The electrode may be mono-polar, bipolar or multi-polar. In order to minimize the risk of an immune response triggered by the subject against the device and minimize damage such as corrosion and the like to the device from other biological fluids, etc., the electrode and any wires and optional housing materials are made of inert materials such as for example silicon, metal, plastic and the like. For example, a multi-polar electrode having about four exposed contacts (e.g., cylindrical contacts may be employed.

A variety of methods may be used to endoscopically or surgically implant the electrode on or adjacent at least a portion of the autonomic nervous system such as on or adjacent one or more nerve fibers of the parasympathetic nervous system and/or sympathetic system, where such methods are known to those of skill in the art. Because some nerve fibers may be in very close proximity to one another within a very small area, an analogous technique may generally be employed to provide operable placement of the electrode on or adjacent to any targeted area of the autonomic nervous system.

A controller or programmer is also typically included in an electrical energy supplying device. The programmer is typically one or more microprocessors under the control of a suitable software program. Other components of the programmer will be apparent to those of skill in the art, e.g., analog to digital converter, etc.

The electric energy supplying device employed in the practice of the subject methods may be pre-programmed for desired parameters. In many embodiments the parameters are controllable such that the electrode signal may be remotely modulated to desired settings without removal of the electrode from its targeted position. Remote control may be performed, e.g., using conventional telemetry with an implanted electric signal generator and battery, an implanted radiofrequency receiver coupled to an external transmitter, and the like. In certain embodiments, some or all parameters of the electrode may be controllable by the subject, e.g., without supervision by a physician. For example, a magnetic signal may be employed. In such embodiments, one or more magnets may be employed such that upon bringing a magnet in proximity to or away from the power source such as a pulse generator, the magnet may be employed to interfere with the electronic circuitry thus modulating the power—either increasing or decreasing the power supplied depending on whether the magnet is brought in proximity or moved away from the power source.

The present invention may be operated as an open-loop controlled system. In an open-loop system, the physician or patient may at any time manually or by the use of pumps or motorized elements adjust treatment parameters such as pulse amplitude, pulse width, pulse frequency, or duty cycle. Optionally, the present invention may incorporate a closed-loop control system which may automatically adjust the electrical parameters in response to a sensed symptom or an important related symptom indicative of the extent of the condition being treated. Under a closed-loop feedback system to provide automatic adjustment of parameters of the electrodes, a sensor that senses a condition of the body is utilized. In certain embodiments, such a condition may be a particular phase of the menstrual cycle (e.g., may sense hormonal changes or the like). More detailed descriptions of sensors that may be employed in the practice of the subject invention, and other examples of sensors and feedback control techniques that may be employed are disclosed in U.S. Pat. No. 5,716,377, which is incorporated herein by reference.

Operative placement of a suitable electric energy supplying device may be accomplished using any suitable technique. In general, such placement includes localization of an area of the autonomic nervous system, positioning the electrode on or adjacent the area and attaching the electrode to a power source. However, with regard to attaching the electrode to a power source, it should be understood that electrodes may be employed which make the implantation and/or attachment of a separate power source unnecessary. For example, an electrode may be employed which includes its own power source, e.g., which is capable of obtaining sufficient power for operation from surrounding tissues in the patient's body or which may be powered by bringing a power source external to the patient's body into contact with the patient's skin, or may include an integral power source, and the like. In such instances, the surgical procedure may be completed upon implantation of the electrode on or adjacent to the area of interest.

An electrode introducer needle may be employed to implant the electrode on or proximate to the area of interest. The size of the introducer needle may vary depending on the diameter of the electrode, etc., where in certain embodiments the electrode introducer needle may be a 12-gauge, 14-gauge, 16-gauge, 18-gauge, 20-gauge needle or 22-gauge needle, e.g., an electrode introducer needle available from Radionics in the Sluyter-Mehta kit as SMK 100 mm 2 mm active tip cannula. However, it should be understood that other electrode introducer needles may be used as appropriate to the needs and skill level of the practitioner performing the surgical procedure.

At least one imaging apparatus such as a CT scan, MRI apparatus, ultrasound apparatus, fluoroscope, or the like, may be employed to monitor the surgical procedure during the localization of a given area, e.g., to assist in determining a suitable entry point for the insertion of the electrode.

Once the entry point is determined, the skin overlying the entry point is shaved and prepared with antiseptic solution. A 25-gauge needle may be used to inject a subcutaneous local anesthetic (such as, for example, 2 cc of 2% lidocaine) into the skin and subcutaneous tissues overlying the entry point. In addition to the local anesthetic, the patient may be given intravenous sedation and prophylactic antibiotics prior to commencement of the implantation procedure if desired.

The electrode introducer needle is inserted at the entry point and advanced. The fluoroscope may be adjusted as the needle is advanced. Once the needle is suitably positioned, the stylet is withdrawn from the electrode introducer needle. A "test" electrode, if employed, used to test the placement of the electrode introducer needle may then be positioned within the central channel of the needle. If a "test" electrode is not employed, the electrode that is to be employed to modulate the autonomic nervous system may then be positioned within the central channel of the needle. The electrode may then be advanced to the distal tip of the needle to place the electrode on or proximate to the area of interest.

In certain embodiments, the "test" electrode, if employed, may be a radiofrequency stimulating electrode suitable to electrically stimulate the tissue at the end of the tip of the electrode and verify its position physiologically within the patient, which may be a different electrode than that ultimately implanted within the patient. A suitable radiofrequency stimulating electrode may be 10 cm with a 2-mm non-insulated active tip. Once the "test" electrode is inserted through the electrode introducer needle with its electrical contacts exposed, it may then be connected to an electrical stimulus/lesion generator for electrical stimulation.

The frequency of stimulation may be set at any suitable frequency, e.g., at about 50 Hz, and the voltage may be gradually increased until the subject reports tingling commensurate with stimulation of or about the area of interest of the autonomic nervous system. Repositioning of the electrode may be performed as necessary.

If a "test" electrode is employed to test the placement of the electrode introducer needle and as such is different from the electrode to be employed to modulate the autonomic nervous system (i.e., the electrode to be implanted if it is desired to implant the electrode that will be employed to modulate the autonomic nervous system), the "test" electrode may then be removed from the electrode introducer needle while the needle is held firmly in place to prevent displacement. The electrode to be implanted may then be inserted through the central channel of the needle while the needle is held in place at the hub. Once the electrode to be implanted is in position, fluoroscopic imaging and electrical stimulation may be employed to verify the correct positioning of the needle and the electrode. Alternatively, if the electrode used to test the placement of the electrode introducer needle is the electrode to be implanted, the electrode should be left in the final test position.

Once the implanted electrode is in place, the end of the electrode that is outside the skin is carefully held in place against the skin. The electrode introducer needle may then be slowly removed, leaving the implanted electrode in place. At this point, if desired, a few small subcutaneous sutures may be placed around the electrode to hold it in the desired position.

Once the needle has been completely removed and the implanted electrode is in the final position, then the proximal part of the electrode that is coming out of the skin may be secured to the skin of the subject, e.g., by adhesive tape. Additionally, a small incision may be made on the skin at the area the electrode exits the body. Then several subcutaneous sutures may be placed around the electrode to hold it in place. The distal end of the electrode may then be connected to an extension wire or catheter, which is tunneled to the subclavicular area, or another region which will house the device used as an energy source for the implanted electrode. The device or devices used to control or stimulate the electrode may be surgically implanted in the desired region by procedures known in the art, such as have been applied in surgical neuromodulation therapies used to treat Parkinson's disease.

Analogous to that described above for pharmacological modulation, embodiments employing electrical modulation typically include determining (e.g., predetermining) the occurrence of one or more phases of a subject's menstrual cycle, where such may be accomplished by any suitable method as described above.

Regardless of how the autonomic nervous system is modulated, certain embodiments of the subject methods may also include detecting, monitoring, observing, etc., information related to one or more aspects of the autonomic nervous system such as a physical and/or chemical aspect, e.g., activity, balance, etc., in at least a portion of the autonomic nervous system, e.g., in at least a portion of the sympathetic nervous system and/or parasympathetic system, and evaluating this information to determine the state of the autonomic nervous system, e.g., the parasympathetic activity and/or sympathetic activity. Once the state of the autonomic nervous system is determined, it may be evaluated in regards to whether the autonomic nervous system is in need of modulation, i.e., whether the sympathetic activity/parasympathetic activity ratio needs to be increased to treat a fertility condition such that this analysis may be employed as a "trigger" to modulating or further modulating at least a portion of the autonomic nervous system wherein modulation may not be otherwise performed unless the analysis determined such is necessary.

Accordingly, collecting and evaluating this type of data and relating it to whether sympathetic activity modulation is required may be employed as a "trigger" to pharmacologically modulating at least a portion of the autonomic nervous system (e.g., performed prior to, during or following a particular autonomic nervous system modulation protocol whether performed using pharmacological methods, electrical energy methods or other methods) such that such data may indicate whether, when, etc., modulation is required—if at all. For example, in certain embodiments modulation of at least a portion of a subject's autonomic nervous system may not be performed unless one or more aspects of the autonomic nervous system are detected and indicate such modulation is necessary. Any suitable physical and/or chemical aspect or indicator of the autonomic nervous system may be employed, e.g., amounts of T helper cells (Th1 and/or Th2), conduction, catecholamine levels, heart rate variability ("HRV"), action potentials, QT interval, as well as chronotropic, inotropic, and vasodilator responses, particular hormonal levels, e.g., associated with a particular phase of the menstrual cycle. In certain embodiments, detection may include detecting the activity or function of a particular organ or system under the control of the autonomic nervous system. Any suitable detection means may be employed to detect relevant information about the autonomic nervous system.

In certain embodiments, a control feedback loop is provided. For example, during or following a particular treatment regimen, the sympathetic activity and/or parasympathetic activity may be monitored, observed, detected, etc., e.g., by sensing conduction in at least a portion of the sympathetic system and/or parasympathetic system by any suitable method. Other methods that may be employed to monitor the autonomic system include, but are not limited to, amounts of T helper cells (Th1 and/or Th2), neurography, continuous or serial measurements of circulating catecholamine levels, chronotropic, inotropic, and vasodilator responses, heart rate variability ("HRV"), particular hormonal levels, e.g., associated with a particular phase of the menstrual cycle, post-ganglionic action potentials, QT interval, and the like (see for example Rang S, Wolf H, Montfrans G A, Karemaker J M. Non-invasive assessment of autonomic cardiovascular control in normal pregnancy and pregnancy-associated hypertensive disorders: a review. J Hypertens 2002; 20(11):2111-9). For example, a sensor suitable for detecting nerve cell or axon activity that are related to the autonomic nervous system may be implanted in a portion of a subject's body. A sensor may take the form of an electrode or the like. Signals received by such a sensor may be amplified before further processing. A sensor may also take the form of a device capable of detecting nerve compound action potentials or may take the form of a transducer that includes an electrode with an ion selective coating applied which is capable of directly transducing the amount of a particular transmitter substance or its breakdown by-products. Embodiments include utilizing a feedback system in such a manner that, if the desired decrease in sympathetic activity is not achieved, the same or a different treatment protocol may be administered. In other words, in utilizing such a feedback system, if the desired increase or decrease in activity or level of sympathetic activity and/or parasympathetic activity is not achieved, the same or different protocol for modulating the activity of the autonomic nervous system activity may be performed. For example, in those instances where a different protocol is performed from a first, pharmacological modulation protocol, one or more of the treatment parameters may be modified, e.g., a different pharmacological agent may be employed instead or in addition to the first, where the differences may include dosage, type, mode of administration, etc. In those instances where a different protocol is performed from a first, electrical energy modulation protocol, one or more of the treatment parameters may be modified, e.g., a different pharmacological agent may be employed instead or in addition to the first, where the differences may include voltage, frequency, pulse width, etc.

Certain embodiments may include simultaneously monitoring, detecting, observing, etc., (i.e., in "real time") the sympathetic activity and/or parasympathetic activity such that modulation of at least a portion of the autonomic nervous system may be performed to treat a fertility condition and the result of the modulation may be observed and/or monitored, e.g., at least once, continuously or intermittently or periodically and in certain embodiments until the desired inhibition in activity (sympathetic activity/parasympathetic activity ratio) is observed or longer. Still further, in many embodiments once the desired autonomic nervous system modulation is achieved the same or different modulation treatment protocol may be performed thereafter at least one time and may be for a period of time, e.g., one or more times, to maintain the desired state such that embodiments of the subject methods may be repeated one or more times.

Electrical modulation may be performed at any suitable time. For example, electrical modulation may be performed at or near the time of a particular phase of a subject's menstrual cycle, i.e., in close temporal proximity to, including during, one or more phases of a subject's menstrual cycle. For example, embodiments of the subject methods may include electrically modulating at least a portion of a subject's autonomic nervous system to achieve a particular sympathetic activity/parasympathetic activity ratio during at least a portion of the menses phase and/or follicular phase and/or the ovulation phase and/or the luteal phase. Of interest is electrical modulation at least near the time of, or during at least a portion of, the luteal phase to modulate the autonomic nervous system to increase the sympathetic activity/parasympathetic activity ratio, e.g., to provide a suitable sympathetic dominance relative to the parasympathetic system, to treat the fertility condition of interest. For example, embodiments may include electrical modulation of at least a portion of the autonomic nervous system to increase the sympathetic activity/parasympathetic activity ratio during the luteal phase, after ovulation. Electrical modulation of at least a portion of the autonomic nervous system to increase the sympathetic activity/parasympathetic activity ratio may be performed before and/or during and/or after insemination, e.g., prior to, during and/or after artificial insemination.

As such, embodiments of the subject invention may include electrically modulating at least a portion of a subject's autonomic nervous system at least one time during ovulation and/or at least one time during the luteal phase to increase the sympathetic activity/parasympathetic activity ratio, where embodiments may include electrically modulating at least a portion of a subject's autonomic nervous system during about all of the days of a subject's luteal phase. In such instances, the subject methods typically include determining the occurrence of the phases of a subject's menstrual cycle by any suitable method, e.g., using hormone-specific blood tests, urine tests, etc., as is known to those of skill in the art. For example, the onset of the luteal phase may be determined using a urine leutinizing hormone ("LH") detection test or kit, as are known in the art, e.g., as available under the brand names OVUQUICK ONE-STEP, CLEARPLAN EASY and SURESTEP. Regardless of the particular method employed, the onset of ovulation and/or the luteal phase may be determined and electrical modulation at least a portion of the subject's autonomic nervous system as described above may be performed at or near the determined start of a subject's luteal phase and/or during at least part of a subject's determined luteal phase.

The above-described methods find use in a variety of different applications, representative types of which are described in greater detail below.

Utility

The subject methods find use in a variety of applications in which it is desired to treat a subject for a fertility condition caused by, affected or otherwise influenced by the subject's autonomic nervous system. In such methods, at least a portion of a subject's autonomic nervous system is modulated to increase the sympathetic activity/parasympathetic activity ratio.

The subject methods find use in the treatment of a variety of different fertility conditions, including, but not limited to, infertility, subfertility, early pregnancy loss, spontaneous abortion, implantation failure, amenorrhea, luteal insufficiency (also referred to as luteal phase defect ("LPD")), dysmenorrhea (also referred to as pelvic pain, menstrual cramps, and the like), chemical pregnancy loss, stillbirth, habitual abortion, endometriosis, and the like. Infertility is defined broadly as the inability to conceive a child despite trying for one year during which there has been intercourse and no use of contraception. Subfertility is defined broadly as the inability to conceive a child after two years during which there has been intercourse and no use of contraception. Early pregnancy loss is defined broadly as the termination of pregnancy without human interference before 20 weeks gestation or below a fetal weight of 500 grams. Spontaneous abortion is defined broadly as the loss of fetus without human interference. Implantation failure is defined broadly as failure of a fertilized egg to implant. Amenorrhea is defined broadly to include the absence of a menstrual period and includes women who have not had a period in their teenage years and women who used to have a regular period that has stopped. Luteal insufficiency is defined broadly as hormonal imbalance during the luteal phase which interferes with fertility. Dysmenorrhea is defined broadly as menstrual cramps. Chemical pregnancy loss is defined broadly as loss of a biochemically evident pregnancy. Stillbirth is defined broadly as pregnancy loss after 20 weeks gestation; neonatal loss is the death of a liveborn fetus. Habitual or recurrent abortion is defined broadly as three or more consecutive abortions. Endometriosis is defined broadly as a condition in which endometrial tissue, the tissue that lines the inside of the uterus, grows outside the uterus and attaches to other organs in the abdominal cavity such as the ovaries and fallopian tubes.

By "treatment" is meant that at least an amelioration of the symptoms associated with the condition afflicting the subject is achieved, where amelioration is used in a broad sense to refer to at least a reduction in the magnitude of a parameter, e.g., symptom, associated with the condition being treated. As such, treatment also includes situations where the condition, or at least symptoms associated therewith, are completely inhibited, e.g. prevented from happening, or stopped, e.g. terminated, such that the subject no longer suffers from the condition, or at least the symptoms that characterize the condition.

A variety of subjects are treatable according to the subject methods. In many embodiments the subjects are "mammals" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects are humans and particularly female humans. As the subject methods are employed to treat fertility disorders, female, humans subjects of child-bearing age may be treated according to the present invention. While the present invention may be used for the treatment of a human, female subject, it is to be understood that the subject methods may also be carried-out on other female animal subjects such as, but not limited to, mice, rats, dogs, cats, livestock and horses, etc. Accordingly, it is to be understood that any female subject in need of being treated according to the subject invention is suitable.

Moreover, suitable subjects of this invention include those who have and those who have not previously been afflicted with a fertility condition, those that have previously been determined to be at risk of suffering from a fertility condition, and those who have been initially diagnosed or identified as being afflicted with or experiencing a fertility condition.

Embodiments of the subject invention may include treating a fertility condition by electrical pacing of the sympathetic nerves to promote sympathetic activity in the female pelvic organs such as the ovaries, fallopian tubes, uterus, cervix and vagina. Such electrical modulation may occur at the spinal cord, from the T10 to L2 segments, inferior mesenteric and superior hypogastric plexuses or the pelvic plexus, or may occur at the junction of the sympathetic nerves and the target organ. Embodiments may also include electrical pacing to decrease parasympathetic activity at the area of S234 sacral segments via the interimediolateral columns to the pelvic plexus. Embodiments of the subject invention may include treating a fertility condition by pharmacological modulation of the sympathetic nerves to promote sympathetic activity in the female pelvic organs such as the ovaries, fallopian tubes, uterus, cervix and vagina. Such electrical modulation may occur at the spinal cord, from the T10 to L2 segments, inferior mesenteric and superior hypogastric plexuses or the pelvic plexus, or may occur at the junction of the sympathetic nerves and the target organ. Embodiments may also include pharmacological modulation to decrease parasympathetic activity at the area of S234 sacral segments via the interimediolateral columns to the pelvic plexus.

Modulation of at least a portion of the autonomic nervous system to treat a fertility condition may be performed in side a subject's body (although controls may be located outside a subject's body). Embodiments also include modulation of at least a portion of the autonomic nervous system to treat a fertility condition from outside a subject's body. For example, embodiments may include transvaginal, transcervical laparascopic access to a target site. Such embodiments may include using suitable delivery devices to operatively place electrical pacing devices and/or directly deliver one or more pharmacological agents, e.g., during the luteal phase, after ovulation.

Devices and Systems

The subject invention also includes devices and systems that may be employed in the practice of the subject methods. The subject systems may include an effective amount of at least pharmacological agent. The pharmacological agent may be in any suitable formulation or form. For example, a system may include a pharmacological composition for transdermal administration, e.g., present as an active agent of a transdermal patch, film or the like, an oral dosage form, injection dosage form, etc.

In certain embodiments, the subject systems may also include suitable pharmacological agent delivery means, the particulars of which may be dictated by the particular pharmacological agent employed, e.g., the particular form of the agent such as whether the pharmacological agent is formulated into preparations in solid, semi-solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intraperiactivityal, intradermal, transdermal, intracheal, intravaginal, endocervical, intrathecal, intranasal, intravesicular, on the eye, in the ear canal, etc. Accordingly, certain systems may include a suitable drug delivery device, e.g., a suppository applicator, syringe, I.V. bag and tubing, electrode, an implantable drug delivery device, an electrostimulatory device, and the like.

Systems may also include one or more devices for delivering, e.g., implanting, a component such as a drug delivery device, an electrosurgical device, and the like, to a target site of a subject such as into the body cavity of a subject. For example, an endoscope, introducer needle, and the like, may be provided. Systems may also include one or more imaging or scanning apparatuses such as a fluoroscope, CT scan, and the like.

Embodiments of the subject systems may also include an electrical energy supplying device such that a system according to the present invention may include at least one electrode for electrically modifying at least a portion of a subject's autonomic nervous system. In certain embodiments the electrical energy supplying device may be an implantable device, or at least certain components such as one or more electrodes, may be implantable. Certain embodiments may include a plurality of electrodes, where some or all may be the same or some or all may be different. For example, at least a first electrode may be provide for electrically stimulating at least a portion of the autonomic nervous system and at least a second electrode may be provided for inhibiting activity in at least a portion of the autonomic nervous system. In certain embodiments, a "test" electrode, as described above, may be included in a system. As noted above, such "test" electrodes may be a radiofrequency stimulating electrode. Still further, one or more electrodes may be included in a system which, instead of or in addition to delivering electric impulses to at least a portion of the autonomic nervous system, delivers an autonomic nervous system pharmacological agent to at least a portion of the autonomic nervous system, e.g., may be used to deliver a pharmacological agent. Included may be an energy source such as a battery or generator, where in certain embodiments the energy source may be implantable, and may also include one or more leads or wires for coupling the one or more electrodes to an energy source.

A system for use in practicing the subject methods may also include a suitable detector for detecting one or more physical and/or chemical aspects related to the autonomic nervous system. The detector at least includes data gathering means. Also provided may be data analysis means where such may be a separate component from or integral with data gathering means, but in many embodiments is operatively coupled to data gathering means, e.g., integral with. In use, data related to one or more aspects of the autonomic nervous system may be collected by data gathering means and forwarded to data analysis means which executes steps necessary to process and evaluate the collected data and determine whether the autonomic nervous system is in need of modulation. Such evaluation may include comparing data to reference values, etc. When present, a detector (or data evaluation means if separate) may be operatively coupled to one or more other elements of a given drug delivery means and/or electrical energy supplying device such that results of the determinations of autonomic modulation may automatically trigger (or cease) activation of drug delivery and/or electrical energy to the autonomic nervous system. Suitable detectors include any detector capable of gathering information about the autonomic nervous system and includes both invasive, minimally invasive and non-invasive detectors where in certain embodiments a detector may be an implantable detector. Suitable detectors include, but are not limited to, those capable of collecting data regarding nerve conduction, circulating catecholamine levels, heart rate variability ("HRV"), post-ganglionic action potentials, QT interval, and the like and include, but are not limited to, MRI apparatuses, CT apparatus, hormone level detectors, neurography apparatuses, cardiovascular monitors, sensors including electrodes, etc.

Computer Readable Mediums and Programming Stored Thereon

Any part of the subject methods, e.g., detection, analysis and activation/termination of drug delivery and/or electrical energy including selecting suitable drug delivery parameters and/or electrical parameters, may be performed manually or automatically. For example, the subject invention may include suitable computing means such as suitable hardware/software for performing one or more aspects of the subject methods. For example, one or more aspects of the subject invention may be in the form of computer readable media having programming stored thereon for implementing the subject methods. Accordingly, programming according to the subject invention may be recorded on computer-readable media, e.g., any medium that can be read and accessed directly or indirectly by a computer. Such media include, but are not limited to, computer disk or CD, a floppy disc, a magnetic "hard card", a server, magnetic tape, optical storage such as CD-ROM and DVD, electrical storage media such as RAM and ROM, and the hybrids of these categories such as magnetic/optical storage media. One of skill in the art can readily appreciate how any of the presently known computer readable mediums may be used to provide a manufacture that includes a recording of the present programming/algorithm for carrying out the above-described methodology. Thus, the computer readable media may be, for example, in the form of any of the above-described media or any other computer readable media capable of containing programming, stored electronically, magnetically, optically or by other means. As such, stored programming embodying steps for carrying-out some or all of the subject methods may be transferred to a computer-operated apparatus such as a personal computer (PC) or the like, by physical transfer of a CD, floppy disk, or like medium, or may be transferred using a computer network, server, or other interface connection, e.g., the Internet.

For example, the subject invention may include a computer readable medium that includes stored programming embodying an algorithm for carrying out some or all of the subject methods, where such an algorithm is used to direct a processor or series of processors to execute the steps necessary to perform the task(s) required of it and as such in certain embodiments the subject invention includes a computer-based system for carrying-out some or all of the subject methods. For example, such a stored algorithm may be configured to, or otherwise be capable of, directing a microprocessor to receive information directly or indirectly from data gathering means (i.e., information collected by data gathering means about the autonomic nervous system) and process that information to determine the state of the autonomic nervous system, e.g., the activity level of the parasympathetic system and/or the sympathetic system and even whether the autonomic nervous system requires modulation and, if so, the specifics of the modulation that may be required, e.g., to treat a fertility condition. The result of that processing may be communicated to a user, e.g., via audio and/or visual means, e.g., the algorithm may also include steps or functions for generating a variety of autonomic nervous system profile graphs, plots, etc.

The algorithm may be configured to, or otherwise be capable of, directing a microprocessor to activate, i.e., turn "on" and "off" a drug delivery device, e.g., an implantable or external drug delivery device and/or an electrical energy supplying device for applying energy to at least a part of the autonomic nervous system, e.g., in response to the above-described determination of the state of the autonomic nervous system. For example, if it is determined that sympathetic activity needs to be increased, the processor may direct a drug delivery device to provide the appropriate amount of drug or otherwise execute a suitable drug treatment regime to result in the desired action. Likewise, in embodiments employing electrical modulation, if it is determined that sympathetic activity needs to be increased, the processor may direct an electrical energy supplying device to provide the appropriate electric impulse or otherwise execute a suitable electric energy treatment regime to result in the desired action The subject invention may also include a data set of known or reference information stored on a computer readable medium to which autonomic nervous system data collected may be compared for use in determining the state of the autonomic nervous system. The data may be stored or configured in a variety of arrangements known to those of skill in the art.

Kits

Also provided are kits for practicing the subject methods. The subject kits may vary greatly in regards to the components included depending on the particular condition treated, method of autonomic nervous system modulation, etc. For example, kits may include one or more pharmacological agents in suitable form(s). A given pharmacological agent may be present in a kit in varying dosages. A kit may also include more than type of pharmacological agent. The dosage amount of the one or more pharmacological agents provided in a kit may be sufficient for a single application or for multiple applications.

In certain embodiments, multiple dosage amounts of a pharmacological agent may be present in a kit. In those embodiments having multiple dosage amounts, such may be packaged in a single container, e.g., a single tube, bottle, vial, and the like, or one or more dosage amounts may be individually packaged such that certain kits may have more than one container of a pharmacological agent.

Suitable means for delivering one or more pharmacological agents to a subject may also be provided in a subject kit. The particular delivery means provided in a kit may be dictated by the particular pharmacological agent employed, as describe above, e.g., the particular form of the agent such as whether the pharmacological agent is formulated into preparations in solid, semi-solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intravaginal, endocervical, intrathecal, intranasal, intravesicular, on the eye, in the ear canal, intraperiactivityal, intradermal, transdermal, intracheal, etc. Accordingly, certain systems may include a suppository applicator, syringe, I.V. bag and tubing, electrode, transdermal patch or film, etc.

Kits may also include diagnostic or detection tests for detecting the occurrence or onset of a particular phase of a subject's menstrual cycle, e.g., by determining certain hormone levels, including relative hormone levels. For example, a urine leutinizing hormone ("LH") detection test or kit or the like may be present in a kit. Urine LH detection kits are known in the art, e.g., OVUQUICK ONE-STEP, CLEARPLAN EASY and SURESTEP brand detection tests.

Kits may also include one or more pregnancy tests for determining whether a female is pregnant or not. For example, a pregnancy test may allow detection of a small amount of a certain hormone, e.g., hCG, as an indicator of pregnancy.

Kits may also include an electrical energy supplying device, as described above. Accordingly, subject kits may include an energy supplying device such that they may include at least one electrode for electrically modifying at least a portion of a subject's autonomic nervous system in accordance with the subject invention, as described above. In certain embodiments, the energy supplying device provided in a kit is an implantable device, or at least certain components such as one or more electrodes, may be implantable. Certain kits may include a plurality of electrodes, where some or all may be the same or some or all may be different. For example, certain kits may include at least a first electrode for electrically modulating activity at least a portion of the sympathetic system and at least a second electrode for electrically modulating activity in at least a portion of the parasympathetic system. In certain embodiments, a subject kit may include a "test" electrode, as described above such as a radiofrequency stimulating electrode. Still further, one or more electrodes may be included in a kit which, instead of or in addition to delivering electric impulses to at least a portion of the autonomic nervous system, delivers an autonomic nervous system pharmacological agent to at least a portion of the autonomic nervous system. Kits according to the subject invention typically also include an energy source such as a battery or generator, where in certain embodiments the energy source may be implantable, and may also include one or more leads or wires for coupling the one or more electrodes to an energy source.

Devices for delivering, e.g., implanting, an electrical energy supplying device and/or a drug delivery device to a target site of a subject such as into the body cavity of a subject may also be included in the subject kits. For example, an endoscope, introducer needle, and the like may be provided.

The subject kits may also include instructions for how to practice the subject methods. For example, instructions may include how to administer the one or more pharmaceutical agents provided in the kit to treat a subject for a fertility condition by pharmacologically modulating at least a portion of the subject's autonomic nervous system. Instructions may include how to use an energy supplying device provided in the kit to treat a subject for a fertility condition by electrically modulating at least a portion of the subject's autonomic nervous system. The instructions are generally recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

It is evident from the above discussion that the above described invention provides methods, system and kits for treating a subject for a condition caused by an autonomic nervous system abnormality in a subject which are easy to use, effective, and which may be used to treat variety of different fertility conditions. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of treating a female subject for a fertility condition, said method comprising:

providing a female subject known to suffer from said fertility condition; and modulating at least a portion of the autonomic nervous system of said female subject to increase the sympathetic activity/parasympathetic activity ratio of said subject in a manner effective to treat said female subject for said fertility condition, wherein said method further comprises determining said sympathetic activity/parasympathetic activity ratio at least prior to said modulation and performing said modulation of said at least one portion of the autonomic nervous system based on the determined sympathetic activity/parasympathetic activity ratio.

2. The method of claim 1, wherein said modulation is performed during at least one predetermined phase of said subject's menstrual cycle.

3. The method of claim 2, wherein said predetermined phase is the luteal phase.

4. The method of claim 1, wherein said increase of the sympathetic activity/parasympathetic activity ratio comprises increasing sympathetic activity.

5. The method of claim 1, wherein said increase of the sympathetic activity/parasympathetic activity ratio comprises decreasing parasympathetic activity.

6. The method of claim 1, wherein said increase of the sympathetic activity/parasympathetic activity ratio comprises increasing sympathetic activity and decreasing parasympathetic activity.

7. The method of claim 1, wherein said modulation is localized.

8. The method of claim 7, wherein said modulation is localized to at least one pelvic nerve.

9. The method of claim 1, wherein said modulation is accomplished by at least applying electrical energy to said at least one portion of said autonomic nervous system.

10. The method of claim 9, wherein said application of electrical energy comprises electrically increasing activity in at least one portion of said autonomic nervous system.

11. The method of claim 9, wherein said application of electrical energy comprises electrically inhibiting activity in at least one portion of said autonomic nervous system.

12. The method of claim 1, wherein said modulation is accomplished by at least administering an effective amount of at least one pharmacological agent to said subject.

13. The method of claim 12, wherein said at least one pharmacological agent is chosen from: beta agonists, alpha agonists, prednisone, steroids, indirect agents that include norepinephrine, epinephrine, norepinephrine, acetyicholine, sodium, calcium, angiotensin I, angiotensin II, angiotensin converting enzyme I, angiotensin converting enzyme II, aldosterone, potassium channel blockers, magnesium channel blockers, cocaine, amphetamines, ephedrine, terbutaline, dopamine, doputamine, antidiuretic hormone, oxytocin, THC cannabinoids, and combinations thereof.

14. The method of claim 12, wherein said method comprises combining said at least one pharmacological agent with seminal fluid to provide an at least one pharmacological agent containing seminal fluid mixture and administering said mixture to said subject.

15. The method of claim 1, wherein said method further comprises determining said sympathetic activity/parasympathetic activity ratio at least during said modulation.

16. The method of claim 1, wherein said method further comprises determining said sympathetic activity/parasympathetic activity ratio at least following said modulation.

17. The method of claim 1, further comprising determining the ratio of Th-1 activity/Th-2 activity.

18. The method of claim 1, wherein said fertility condition is infertility.

19. The method of claim 1, wherein said infertility condition is subfertility.

20. The method of claim 1, wherein said fertility condition is early pregnancy loss.

21. The method of claim 1, wherein said fertility condition is spontaneous abortion.

22. The method of claim 1, wherein said fertility condition is an implantation failure.

23. The method of claim 1, wherein said fertility condition is amenorrhea.

24. The method of claim 1, wherein said fertility condition is luteal insufficiency.

25. The method of claim 1, wherein said fertility condition is dysmenorrhea.

26. The method of claim 1, wherein said fertility condition is chemical pregnancy loss.

27. The method of claim 1, wherein said fertility condition is stillbirth.

28. The method of claim 1, wherein said fertility condition is habitual abortion.

29. The method of claim 7, wherein said modulation is localized to an area of the autonomic nervous system selected from the group consisting of pre-ganglionic nerve fibers, post-ganglionic nerve fibers, ganglionic structures, efferent nerve fibers, and afferent nerve fibers.

30. The method of claim 1, wherein said sympathetic activity/parasympathetic activity ratio is determined by sensing conduction in at least a portion of the sympathetic and/or parasympathetic nervous system.

31. The method according to claim 1, wherein said modulation comprises an implanted electrical energy delivering device.

32. The method according to claim 31, wherein said implanted device is an electrode.

33. The method according to claim 5, wherein said decrease in parasympathetic activity comprises electrical inhibition of at least one portion of the parasympathetic nervous system.

34. The method according to claim 33, wherein said electrical inhibition comprises ablation.

35. The method according to claim 1, wherein said modulation is performed for a period of days.

36. The method according to claim 1, wherein said modulation is performed for a period of weeks.

* * * * *

UNITED STATES PATENT AND TRADEMARK OFFICE
CERTIFICATE OF CORRECTION

PATENT NO. : 7,676,269 B2
APPLICATION NO. : 10/748976
DATED : March 9, 2010
INVENTOR(S) : Anthony Joonkyoo Yun It is certified that error appears in the above-identified patent and that said Letters Patent is hereby corrected as shown below:

In Claim 13, Column 38, line 48, replace the word "acetyicholine" with the word acetylcholine.

Signed and Sealed this

Twelfth Day of October, 2010

David J. Kappos
*Director of the United States Patent and Trademark Office*